US007582748B2

(12) United States Patent
Rabi

(10) Patent No.: US 7,582,748 B2
(45) Date of Patent: Sep. 1, 2009

(54) METHODS OF MANUFACTURE OF 2'-DEOXY-β-L-NUCLEOSIDES

(75) Inventor: Jaime A. Rabi, Rio de Janeiro (BR)

(73) Assignee: Microbiologica Quimica E Farmaceutical Ltd., Rio de Janeiro (BR)

( * ) Notice: Subject to any disclaimer, the term of this patent is extended or adjusted under 35 U.S.C. 154(b) by 0 days.

(21) Appl. No.: 10/806,296

(22) Filed: Mar. 22, 2004

(65) Prior Publication Data
US 2004/0266996 A1 Dec. 30, 2004

Related U.S. Application Data

(60) Provisional application No. 60/456,465, filed on Mar. 20, 2003.

(51) Int. Cl.
C07H 1/00 (2006.01)
(52) U.S. Cl. .................................... 536/124; 536/1.11
(58) Field of Classification Search ................. 536/1.11, 536/124
See application file for complete search history.

(56) References Cited

U.S. PATENT DOCUMENTS

| | | | |
|---|---|---|---|
| 3,891,623 | A | 6/1975 | Vorbruggen et al. |
| 4,754,026 | A | 6/1988 | Kawada et al. |
| 4,957,924 | A | 9/1990 | Beauchamp |
| 5,144,018 | A | 9/1992 | Kuzuhara et al. |
| 5,565,438 | A | 10/1996 | Chu et al. |
| 5,567,688 | A | 10/1996 | Chu et al. |
| 5,587,362 | A | 12/1996 | Chu et al. |
| 6,153,594 | A | 11/2000 | Børretzen et al. |
| 6,248,878 | B1 | 6/2001 | Matulic-Adamic et al. |
| 6,271,212 | B1 | 8/2001 | Chu et al. |
| 6,395,716 | B1 | 5/2002 | Gosselin et al. |
| 6,444,652 | B1 * | 9/2002 | Gosselin et al. ............... 514/45 |
| 6,566,344 | B1 | 5/2003 | Gosselin et al. |
| 6,569,837 | B1 | 5/2003 | Gosselin et al. |
| 2003/0050229 | A1 | 3/2003 | Sommadossi et al. |
| 2003/0083306 | A1 | 5/2003 | Imbach et al. |
| 2004/0006002 | A1 | 1/2004 | Sommadossi et al. |
| 2005/0020825 | A1 | 1/2005 | Storer et al. |

FOREIGN PATENT DOCUMENTS

| | | |
|---|---|---|
| DE | 0140254 Z | 2/1980 |
| DE | 42 24 737 A1 | 2/1994 |
| EP | 0 352 248 A1 | 1/1990 |
| JP | 62-93645 A | 10/1994 |
| JP | 07224081 A2 | 8/1995 |
| JP | 2000290289 A2 | 10/2000 |
| WO | WO 95/07287 A1 | 3/1995 |
| WO | WO 96/11204 A1 | 4/1996 |
| WO | WO 96/13512 * | 5/1996 |
| WO | WO 96/13512 A2 | 5/1996 |
| WO | WO 96/40164 A1 | 12/1996 |
| WO | WO 00/09531 A2 | 2/2000 |
| WO | WO 01/90121 A2 | 11/2001 |
| WO | WO 01/96353 A2 | 12/2001 |

OTHER PUBLICATIONS

Imbach, J-L. et al, J. Heterocyclic Chem., 1993, 30, 1229-1233.*
Benzaria, S., et al., "Synthesis of potential prodrugs of b-4-L-dC, a potent and selective anti-HBV agent,", Antiviral Res., 50:A79 (2001). [Abstract No. 137].
Bloch, A., et al. "The Role Of The 5'-Hydroxyl Group Of Adenosine In Determining Substrate Specificity For Adenosine Deaminase," J. Med. Chem., 10(5):908-12 (Sep. 1967).
Bryant, M.L., et al., "Antiviral L-nucleosides specific for hepatitis B virus infection," Antimicrob. Agents Chemother., 45(1):229-235 (Jan. 2001).
Budavari, et al., Eds., The Merck Index, 12th Edition, Entry No. 10039, p. 10044.
Cavelier, F., et al., "Studies of selective Boc removal in the presence of silyl ethers," Tetrahedron Letters, 37:5131-5134 (1996).
Cretton-Scott, E., et al., "Pharmacokinetics of β-L-2'-deoxycytidine prodrugs in monkeys," Antiviral Res., 50:A44 (2001) [Abstract No. 16].
Davisson, V.J., et al., "Synthesis of Nucleotide 5'-Diphosphates from 5'-O-Tosyl Nucleosides," J. Org. Chem., 52(9):1794-1801 (1987).
Fox, J.J., et al,. "Thiolation of nucleosides. II. Synthesis of 5-methyl-2'-deoxycytidine and related pyrimidine nucleosides," J. Am. Chem. Soc., 81:178-187 (1959).
Hoard, D.E., et al., "Conversion of Mono- and Oligodeoxyribonucleotides to 5'-Triphosphates," J. Am. Chem. Soc., 87(8):1785-1788 (Apr. 20, 1965).
Holy, A., "Nucleic Acid Components and Their Analogs. CLIII. Preparation of 2'-deoxy-L-Ribonucleosides of the Pyrimidine Series," Collect. Czech. Chem. Commun., 37(12):4072-4087 (1972).
Hubbard, A.J. et al., "An Investigation by 1H NMR Spectroscopy Into the Factors Determining the β :α Ratio of the Product in 2'-Deoxynucleoside Sythesis", Nucleic Acids Research, 12(7) : 6827-6837(1984).
Imai, K., et al., "Studies on Phosphorylation. IV. Selective Phosphorylation of the Primary Hydroxyl Group in Nucleosides." J. Org. Chem., 34(6):1547-1550 (Jun. 1969).
Kaneko, M., et al., "A convenient synthesis of cytosine nucleosides," Chem. Pharm. Bull., 20:1050-1053 (1972).
Kerr, S.G., et al., "N4-(dialkylamino)methylene derivatives of 2'-deoxycytidine and arabinocytidine: physicochemical studies for potential prodrug applications," J. Pharm. Sci., 83(4):582-586 (Apr. 1994).

(Continued)

Primary Examiner—Shaojia Anna Jiang
Assistant Examiner—Ganapathy Krishnan
(74) Attorney, Agent, or Firm—Jones Day

(57) ABSTRACT

The present invention relates to the synthesis of 2'-deoxy-β-L-thymidine, 2'-deoxy-β-L-uridine and 2'-deoxy-β-L-cytidine, and their derivatives, such as the 3'-O-acyl or 3',5'-O-diacyl prodrugs, including the 3'-O-L-aminoacyl and 3',5'-O-L-diaminoacyl prodrugs, and particularly the 3'-O-L-valinyl and 3',5'-O-L-divalinyl prodrugs.

23 Claims, 2 Drawing Sheets

OTHER PUBLICATIONS

Lin, T.-S., et al., "Synthesis of Several Pyrimidine L-Nucleoside Analogues as Potential Antiviral Agents," *Tetrahedron Letters*, 51(4):1055-1068 (1995).

Luh, T.-Y., et al., "A convenient method for the selective esterification of amino-alcohols," *Synthetic Communications*, 8(5):327-333 (1978).

Maga, Giovanni, et al., "Lack of stereospecificity of suid pseudorabies virus thymidine kinase," *Biochem. J.*, 294(2):381-385 (1993).

McCormick, J., et al., "Structure and total synthesis of HF-7, a neuroactive glyconucleoside disulfate from he funnel-web spide *Hololena curta*," *J. Am. Chem. Soc.*, 121(24):5661-5664 (1999).

Pierra, C., et al., "Comparative studies of selected potential prodrugs of β-L-dC, a potent and selective anti-HBV agent," *Antiviral Res.*, 50:A79 (2001). [Abstract No. 138].

Standring, D.N., et al., "Antiviral beta-L-nucleosides specific for hepatitis B virus infection," *Antiviral Chem. & Chemother.*, 12 (Suppl. 1):119-129 (2001).

Tang, X.-Q., et al., "2'-C-Branched ribonucleosides: Synthesis of the phosphoramidite derivatives of 2'-C-b-methylcytidine and their incorporation into oligonucleotides," *J. Org. Chem.*, 64(3):747-754 (1999).

Tyrsted, G., et al. "Inhibition of the synthesis of 5-phosphoribosyl-l-pyrophosphate by 3'-deoxy-adenosine and structurally related nucleoside analogs." *Biochim. Biophys. Acta.*, 155(2):619-622 (Feb. 26, 1968).

Verri, A., et al., "Lack of enantiospecificity of human 2'-deoxycytidine kinase: relevance for the activation of β-L-deoxycytidine analogs as antineoplastic and antiviral agents," *Molecular Pharmacology*, 51(1):132-138 (Jan. 1997).

Verri, A., et al., "Relaxed Enantioselectivity of Human Mitochondrial Thymidine Kinase and Chemo-therapeutic Uses of L-Nucleoside Analogues," *Biochem. J.*, 328(1):317-320 (Nov. 15, 1997).

Von Janta-Lipinski, M., et al., "Newly Synthesized L-Enantiomers of 3'-Fluoro-Modified β-2'-Deoxyribonucleoside 5'-Triphosphates Inhibit Hepatitis B DNA Polymerase but not the Five Cellular DNA Polymerases α, β, γ, δ, and ε Nor HIV-1 Reverse Transcriptase," *J. Medicinal Chemistry*, 41(12):2040-2046 (May 21, 1998).

Zedeck, M.S., et al., "Inhibition of the steroid-induced synthesis of D5-3-ketosteroid isomerase in *Pseudomonas testosterone* by a new purine deoxyribonucleoside analog: 6-chloro-8-aza-9-cyclopentylpurine," *Mol. Pharmacol.*, 3(4):386-395 (1967).

Zhang, W., et al., "Removal of silyl protecting groups from hydroxyl functions with ammonium fluoride in methanol," *Tetrahedron Letters*, 33:1177-1180 (1992).

\* cited by examiner

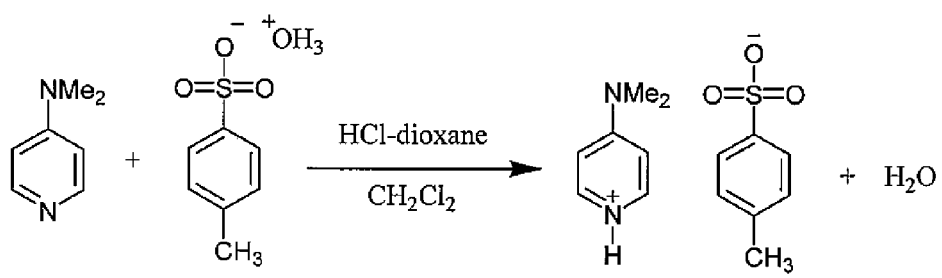
Figure 1: Synthesis of 4-(N,N-dimethylamino)pyridinium 4-toluenesulfonate
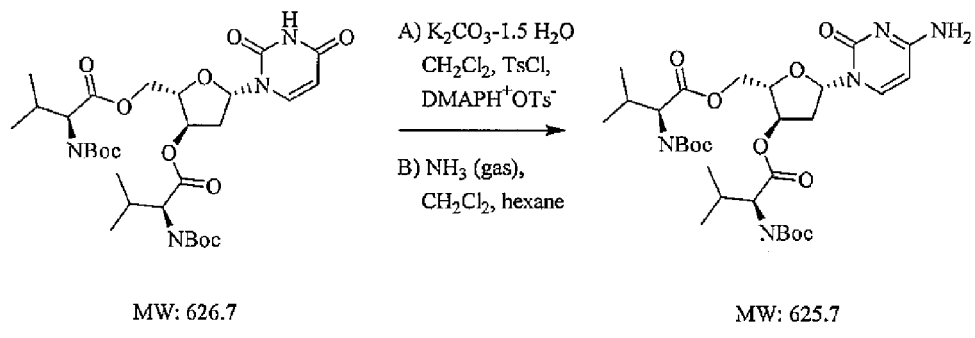
Figure 2: Synthesis of 3',5'-di-(Boc-L-valinyl)-L-2'-deoxycytidine

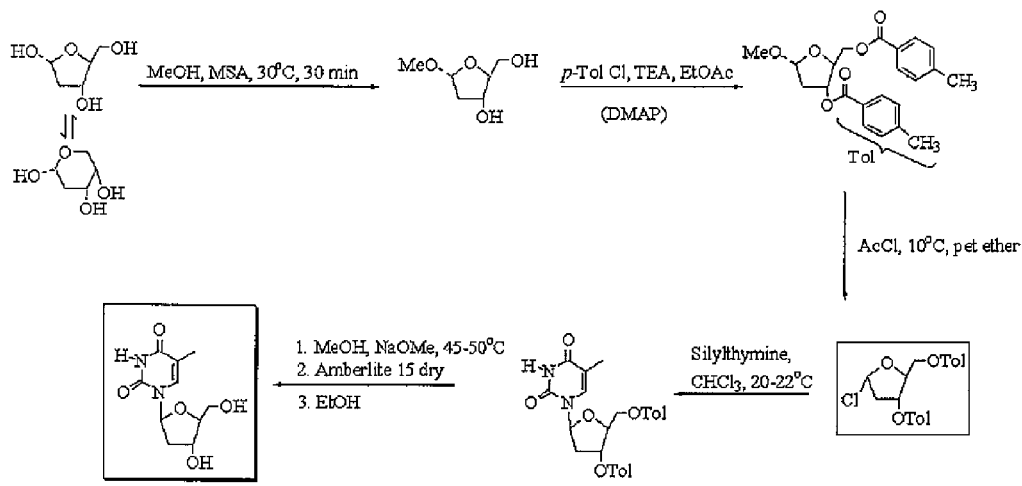
Figure 3: Synthesis of 1-α-chloro-3,5-di-O-toluoyl-2-deoxy-L-ribose and coupling with silylated thymine.
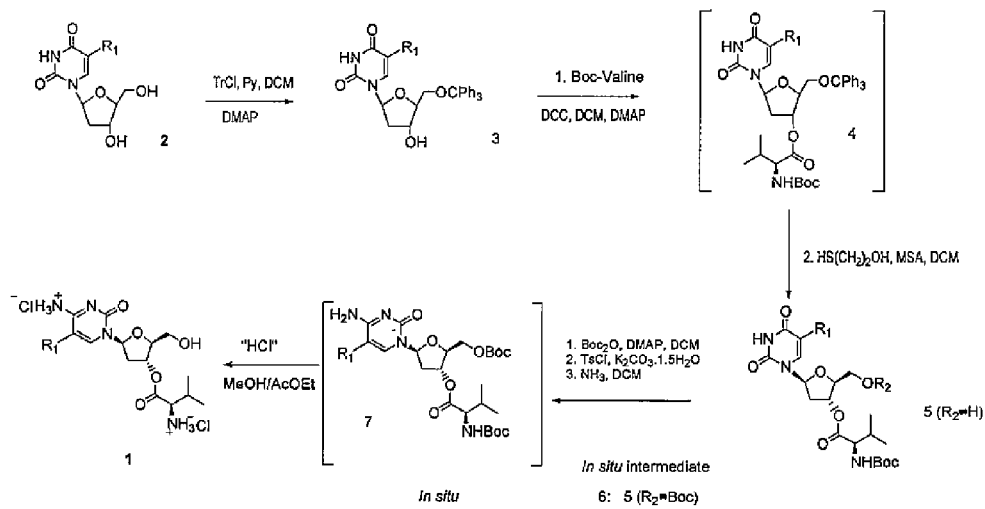
Figure 4: Synthesis of 3'-O-L-valyl-2'-deoxy-β-L-cytidine from 2'-deoxy-β-L-uridine

METHODS OF MANUFACTURE OF 2'-DEOXY-β-L-NUCLEOSIDES

CROSS REFERENCE TO RELATED APPLICATIONS

This application claims priority to U.S. Provisional Application No. 60/456,465, filed Mar. 20, 2003.

FIELD OF THE INVENTION

This invention relates to processes for the production of 2'-deoxynucleosides and their 3'—O-acyl prodrugs, such as their 3'—O-L-aminoacyl and 3',5'—O-L-diaminoacyl prodrugs, useful in the formulation of pharmaceuticals, and in particular for pharmaceuticals for the treatment and/or prevention of viral infections such as hepatitis B virus infection. In particular, the present invention relates to processes for the production of at least an optionally protected 1-halo-2-deoxyribose, β-L-thymidine, β-L-2'-deoxyuridine, β-L-2'-deoxycytidine, 3'—O-L-valyl-2'-deoxy-β-L-cytidine, and 3',5'—O-L-divalyl-2'-deoxy-β-L-cytidine from stable starting materials.

BACKGROUND OF THE INVENTION

HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

A number of synthetic nucleosides have been identified that exhibit activity against HBV. The (−)-enantiomer of BCH-189 (2',3'-dideoxy-3'-thiacytidine), known as 3TC, has been approved for the treatment of hepatitis B. See U.S. Pat. No. 5,532,246 as well as EPA 0 494 119 A1 filed by BioChem Pharma, Inc.

Adefovir (9-{2-(phosphonomethoxy)ethyl}adenine, also referred to as PMEA or ({2-(6-amino-9H-purin-9-yl) ethoxy}methylphosphonic acid), also has been approved in the United States for the treatment of patients infected with hepatitis B virus. See, for example, U.S. Pat. Nos. 5,641,763 and 5,142,051. Resistance to adefovir treatment in patients with HBV has been noted.

β-2-Hydroxymethyl-5-(5-fluorocytosin-1-yl)-1,3-oxathiolane ("FTC"), claimed in U.S. Pat. Nos. 5,814,639 and 5,914,331 to Liotta et al., exhibits activity against HBV. See Furman et al., "The Anti-Hepatitis B Virus Activities, Cytotoxicities, and Anabolic Profiles of the (−) and (+) Enantiomers of cis-5-Fluoro-1-{2-(Hydroxymethyl)-1,3-oxathiolane-5-yl}-Cytosine" *Antimicrobial Agents and Chemotherapy*, December 1992, 2686-2692; and Cheng, et al., *Journal of Biological Chemistry*, 1992, 267 (20), 13938-13942.

U.S. Pat. Nos. 5,565,438, 5,567,688 and 5,587,362 (Chu, et al.) disclose the use of 2'-fluoro-5-methyl-β-L-arabinofuranolyluridine (L-FMAU) for the treatment of hepatitis B and Epstein Barr virus.

Yale University and The University of Georgia Research Foundation, Inc. disclose the use of L-FDDC (5-fluoro-3'-thia-2',3'-dideoxycytidine) for the treatment of hepatitis B virus in WO 92/18517.

WO 96/40164 filed by Emory University, UAB Research Foundation, and the Centre National de la Recherche Scientifique (CNRS) discloses a number of β-L-2',3'-dideoxynucleosides for the treatment of hepatitis B.

WO 95/07287 also filed by Emory University, UAB Research Foundation, and the Centre National de la Recherche Scientifique (CNRS) discloses 2'- or 3'-deoxy and 2',3'-dideoxy-β-L-pentofuranosyl nucleosides for the treatment of HIV infection.

WO096/13512 filed by Genencor International, Inc., and Lipitek, Inc., discloses the preparation of L-ribofuranosyl nucleosides as antitumor agents and virucides.

WO095/32984 discloses lipid esters of nucleoside monophosphates as immuno-suppresive drugs.

DE 4224737 discloses cytosine nucleosides and their pharmaceutical uses.

Idenix Pharmaceuticals, Ltd. discloses 2'-deoxy-L-erythropentofurano-nucleosides, and their use in the treatment of HBV in U.S. Pat. Nos. 6,395,716; 6,444,652; 6,566,344 and 6,539,837. See also WO 00/09531. A method for the treatment of hepatitis B infection in humans and other host animals is disclosed that includes administering an effective amount of a biologically active 2'-deoxy-β-L-erythro-pentofuranonucleoside (alternatively referred to as β-L-dN or a β-L-2'-dN) or a pharmaceutically acceptable salt, ester or prodrug thereof, including β-L-deoxyribothymidine (β-L-dT), β-L-deoxyribocytidine (β-L-dC), β-L-deoxyribouridine (β-L-dU), β-L-deoxyribo-guanosine (β-L-dG), β-L-deoxyriboadenosine (β-L-dA) and β-L-deoxyriboinosine (β-L-dI), administered either alone or in combination, optionally in a pharmaceutically acceptable carrier. 5' and $N^4$ (cytidine) or $N^6$ (adenosine) acylated or alkylated derivatives of the active compound, or the 5'-phospholipid or 5'-ether lipids were also disclosed.

von Janta-Lipinski et al. *J. Med. Chem.*, 1998, 41 (12), 2040-2046 disclose the use of the L-enantiomers of 3'-fluoro-modified β-2'-deoxyribonucleoside 5'-triphosphates for the inhibition of hepatitis B polymerases. Specifically, the 5'-triphosphates of 3'-deoxy-3'-fluoro-β-L-thymidine (β-L-FTTP), 2',3'-dideoxy-3'-fluoro-β-L-cytidine (β-L-FdCTP), and 2',3'-dideoxy-3'-fluoro-β-L-5-methylcytidine (β-L-FMethCTP) were disclosed as effective inhibitors of HBV DNA polymerases. In addition, von Janta-Lipinski et al. discloses the biological activity of the triphosphate of β-L-thymidine (but not β-L-2'-dC) as a nucleoside inhibitor of endogenous DNA polymerases of HBV and DHBV. However, only triphosphorylated β-L-thymidine was evaluated, not the claimed unphosphorylated form, and there is no comment in the article on whether those β-L-nucleosides are phosphorylated in cells or in vivo or, more importantly, there is no comment on the efficacy of phosphorylation of β-L-thymidine in vivo. Because of this, the article does not teach that β-L-thymidine would have any hepatitis B activity in a cell or in vivo. See also WO 96/1204.

European Patent Application No. 0 352 248 A1 to Johansson et al. discloses the use of L-ribofuranosyl compounds for the treatment of hepatitis B.

Verri et al. disclose the use of 2'-deoxy-β-L-erythro-pentofuranonucleosides as antineoplastic agents and as anti-herpetic agents (*Mol. Pharmacol.* (1997), 51(1), 132-138 and *Biochem. J.* (1997), 328(1), 317-20). Saneyoshi et al. demonstrate the use of 2'-deoxy-L-ribonucleosides as reverse transcriptase (I) inhibitors for the control of retroviruses and for the treatment of AIDS, Jpn. Kokai Tokkyo Koho JP06293645 (1994).

Giovanni et al. tested 2'-deoxy-β-L-erythro-pentofuranonucleosides against partially pseudorabies virus (PRV), *Biochem. J.* (1993), 294(2), 381-5.

Chemotherapeutic uses of 2'-deoxy-β-L-erythro-pentofuranonucleosides were studied by Tyrsted et al. (*Biochim. Biophys. Acta* (1968), 155(2), 619-22) and Bloch, et al. (*J. Med. Chem.* (1967), 10(5), 908-12).

Morris S. Zedeck et al. first disclosed β-L-dA for the inhibition of the synthesis of induced enzymes in *Pseudomonas testosteroni*, *Mol. Phys.* (1967), 3(4), 386-95.

In addition, cytosine derivatives are useful as intermediates for production of drugs such as cytidine diphosphate choline whose generic name is Citicoline.

Lin et al. "Synthesis of Several Pyrimidine L-Nucleoside Analogues as Potential Antiviral Agents" *Tetrahedron*, 1995, 51 (4), 1055-1068, discusses that β-L-5-iodo-2'-deoxyuridine (β-L-IUdR, compound 7) is active against herpes infection and various other DNA viruses, that BVdU and β-L-BV-ara-U are also active against herpes, β-L-BV-ara-U is active against varicella-zoster virus; and that 2',3'-dideoxy-L-azacytidine was found to be active against HBV.

U.S. Patent Publication Ser. No. 20030083306 to Idenix Pharmaceuticals, Ltd. discloses 3'-prodrugs of 2'-deoxy-β-L-nucleosides for the treatment of HBV. See also WO 01/96353.

U.S. Pat. No. 4,957,924 to Beauchamp discloses various therapeutic esters of acyclovir.

In the Apr. 17-21, 2002 European Association for the Study of the Liver meeting in Madrid, Spain, Sühnel et al. of Gilead Sciences, Inc. presented a poster indicating that combinations of adefovir with β-L-2'deoxythymidine produce additive antiviral effects against HBV in vitro.

Treatments for hepatitis B infection are also described in Lok and McMahon, AASLD Practice Guidelines, pp. 1225-1241 (2001), including treatment with interferons. Eastern woodchucks chronically infected with the woodchuck hepatitis virus (WHV) were used as a model of HBV infection to study the antiviral effect of 1-(2-fluoro-5-methyl-β-L-arabinofuranosyl)-uracil (L-FMAU) and WHV surface antigen vaccine. The humoral and cellular immunity associated with the combination of L-FMAU and vaccine resembled that observed in self-limited WHV infection. Menne et al., *J. Virology*, 76(11):5305-5314 (2002).

Such therapeutic L-deoxynucleosides can be prepared by any number of routes. The earliest dates back to a synthesis of β-L-2'-deoxycytidine and β-L-2'-deoxythymidine by Holy, "Preparation of 2'-deoxy-L-ribonucleosides of the Pyrimidine Series", *Collect. Czech. Chem. Commun.* (1972), 37(12), 4072-87. This method involves conversion of arabinose to a pyrimidine nucleoside by a multi-step construction of the pyrimidine ring. Because this method is expensive and non-versatile, however, other methods have also been developed. One of the more versatile involves the coupling of a silylated pyrimidine or purine base to an activated deoxyribose. For this method to be successful, the deoxyribose must be activated with a good leaving group at C-1. Further, this leaving group must have the α configuration. This configuration must remain stable throughout the reaction and, in addition, the formation of the N-glycosidic bond with displacement of the leaving group must occur with inversion of the configuration thus leading to the desired β nucleoside. If these conditions are not met, the resulting product is usually a mixture of α and β nucleosides from which it is almost impossible to separate the isomers with methods other than chromatographic.

It is worth noting that even with an appropriate activated 2-deoxy-sugar, the coupling with silylated cytosines does not occur with acceptable stereoselectivity. As a result, cytosine nucleosides are better made from their corresponding uracil analogs.

For the large scale synthesis of 3'-aminoacyl-2'-deoxycytidines, it was necessary to consider the amination procedure of its uracil nucleoside precursor. Thus, it became necessary to develop a very mild procedure that preserved the identity of the amino acid moiety leading to an intermediate which would be easily purified before releasing the desired prodrug in pure form. In this case, too, the method should be versatile. It should produce high yields of final product and intermediates, and these should be stable, easy to handle, and easily scaled to commercial size.

Several attempts to convert relatively inactive uridine to cytidine have been attempted. Within WO 00/09531, they obtained various 2'-deoxy-β-L-erythro-pentofuranonucleoside derivatives by procedures well known in the art and can be prepared according to the method disclosed by Holy, Collect. Czech. Chem. Commun. (1972), 37(12), 4072-87 and Mol. Phys. (1967), 3(4), 386-95. In addition, mono, di, and triphosphate derivatives of the active nucleosides can be prepared as described according to published methods. The monophosphate can be prepared according to the procedure of Imai et al., J. Org. Chem., 34(6), 1547-1550 (June 1969). The diphosphate can be prepared according to the procedure of Davisson et al., J. Org. Chem., 52(9), 1794-1801 (1987). The triphosphate can be prepared according to the procedure of Hoard et al., J. Am. Chem. Soc., 87(8), 1785-1788 (1965).

Then, they were able to convert uridine derivatives to cytidine derivatives using Lawesson's reagent.

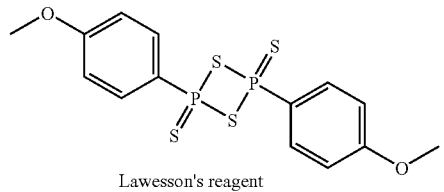

Lawesson's reagent

Lawesson's reagent was added to a solution of 1-(3,5-di-O-benzoyl-2-deoxy-β-L-erythro-pentofuranosyl)uracil in anhydrous 1,2-dichloroethane and the reaction mixture was stirred under reflux for 2 h. The solvent was then evaporated under reduced pressure and the residue was purified by silica gel column chromatography to give the 4-thio intermediate as a yellow foam. A solution of this thio-intermediate (1.5 g, 3.31 mmol) in methanolic ammonia (previously saturated at −10° C. and tightly stopped) (50 mL) was heated at 100° C. in a stainless-steel bomb for 3 h and then cooled to 0° C. The solution was evaporated under reduced pressure. The resulting crude material was purified by silica gel column chromatography [eluent: stepwise gradient of methanol(0-20%) in dichloromethane]. Finally, the appropriate fractions were pooled, filtered through a unit Millex HV-4 (0.45 μm, Millipore) and evaporated under reduced pressure to provide the desired 2'-deoxy-β-L-cytidine ("β-L-dC") as a foam (0.6 g, 80%) which was crystallized from absolute EtOH.

This procedure is a derivation of the historic conversion of uridine to cytidine, published in 1959 in J. Amer. Chem. Soc., 81, 178. Traditionally, uridine derivatives with protected hydroxyl groups in the sugar moiety are allowed to react with phosphorus pentasulfide to give 4-thio derivatives. These 4-thio derivatives then can be aminated at the 4-position with ammonia or other materials. Upon deprotection of the sugar hydoxyls, cytidine derivatives can be obtained.

Several other procedures have been proposed to convert uracil glycoside derivatives to cytosine glycoside derivatives. Drs. Helmut Vorbrueggen and Ulrich Niedballa in German Patent No. DE2122991 entitled Verfahren Zur Herstellung von Cytosin-Und 6-Azacytosinnucleosiden (1982) disclose a procedure where uridine or uridine derivatives with protected hydroxyl groups are allowed to react with a silylating agent such as hexamethyldisilazane (HMDS) to give 4—O-trimethyl-silyluridine derivatives. These 4—O-trimethyl-silyluridine derivatives likewise can be aminated at the position 4 with ammonia or other materials and deprotected, to give cytidine derivatives.

In 1972, in Chem. Pharm. Bull., 20, 1050, a procedure was disclosed where uridine with protected hydroxyl groups is subjected to chlorination with phosphorus oxychloride in the presence of diethylaniline hydrochloride as a catalyst to give cytidine.

GDR Pat. No. 140,254 Official Gazette (1980) discloses a procedure where a uridine derivative with protected hydroxyl groups is allowed to react with an organic sulfonylating agent in the presence of sodium hydride to give a 4—O-sulfonyluridine derivative which is then aminated at the position 4 by ammonia, and deprotected, to give cytidine derivatives.

However, these procedures are industrially disadvantageous because of the not necessarily satisfactory yield of the desired substances and of the use of an inflammable agent difficult to handle such as sodium hydride.

U.S. Pat. No. 4,754,026 to Mitsuru Kawada (1988) entitled "Conversion of Uracil Derivatives to Cytosine Derivatives" describes the production of 4—O-sulfonyluridine derivatives by the reaction of uridine derivatives with protected hydroxyl groups in the sugar moiety with organic sulfonylating agents. When anhydrous potassium carbonate was used as an acid-eliminating agent in the sulfonylation, 4—O-sulfonyl derivatives could be obtained almost quantitatively. The specific action of potassium carbonate was surprising, seeing that sulfonylation did not proceed sufficiently with an alkali such as sodium carbonate as the acid-eliminating agent. However, the yield of this reaction is still relatively low if certain protecting groups are employed, or if large scale production is required.

Prodrugs

Pharmaceutically active compounds are sometimes administered in an esterified prodrug form. Carboxylic acid esters are used most commonly, while phosphonate and phosphate esters are used less frequently because they fail to hydrolyze in vivo and may produce toxic byproducts (see U.S. Pat. No. 6,312,662 to Erion et al.). Acyloxyalkyl esters are sometimes used as prodrugs for phosphate and phosphonate compounds, as are cyclic phosphonate esters and aryl esters, especially phenyl and benzyl esters (Farquhar et al., J. Pharm. Sci., (1983), 72(3):324; U.S. Pat. No. 6,312,662 to Erion et al.). Like nucleosides, phosphonic acids such as, for example, phosphonoformic acid and PMEA (Adefovir; 9-(2-phosphonylmethoxy-ethyl)adenine) show antiviral activity as do carboxylic acid or ether lipid prodrugs of nucleosides (U.S. Pat. No. 6,458,773 to Gosselin et al.).

Nucleoside prodrugs have been previously described for the treatment of other forms of hepatitis. WO 01/96353 (filed Jun. 15, 2001) to Indenix Pharmaceuticals, Ltd. discloses 3'-prodrugs of 2'-deoxy-β-L-nucleosides for the treatment of HBV.

U.S. Pat. No. 4,957,924 to Beauchamp discloses various therapeutic esters of acyclovir.

The use of aminoacyl derivatives had already been introduced commercially to improve the properties of Acyclovir. Valacyclovir is in fact the L-valine ester prodrug of acyclovir (MERCK INDEX 12TH EDITION, NUMBER 10039, P10044).

Historically, prodrug syntheses and formulations have typically involved the 5'-position of a nucleoside or nucleoside analogue. Gosselin et al., supra, reported nucleosides in which the H of the 5'—OH group is replaced by any of the following: an acyl group including those in which the non-carbonyl moiety of the ester group is selected from straight, branched, or cyclic $C_1$-$C_{20}$ alkyl, phenyl or benzyl; a naturally-occurring or non-naturally-occurring amino acid; a 5'-ether lipid or a 5'-phosphoether lipid; alkoxyalkyl including methoxymethyl; aralkyl including benzyl; aryloxyalkyl such as, for example, phenoxymethyl; aryl including phenyl, optionally substituted with halogen, $C_1$-$C_4$ alkyl or $C_1$-$C_4$ alkoxy; a dicarboxylic acid such as, for example, succinic acid; a sulfonate ester such as, for example, an alkyl or aralkyl sulphonyl including methanesulfonyl; or a mono-, di-, or triphosphate ester.

Matulic-Adamic et al. (U.S. Pat. No. 6,248,878) reported the synthesis of nucleoside analogues that comprise a ribofuranose ring with a phosphorus-containing group attached to the 3'-position via an oxygen atom and a substituted pyrimidine base. The phosphorus-containing group includes dithioates or phosphoramidites, or may be part of an oligonucleotide. These compounds are prodrugs because they are reacted further to provide final, desired nucleosides and nucleoside analogues. The compounds are synthesized in a multi-step process that couples, as starting materials, a ribofuranose having an hydroxy or acetoxy group at C-1 and benzoyl-protecting groups at C-2-, C-3 and C-5, and a 4-OS-iMe₃ pyrimidine to produce an 1-(2,3,5-tri-O-benzoyl-ribofuranosyl)-pyrimidin-4-one; then adds ammonia in methanol to the product of the first reaction in order to remove the benzoyl protecting groups; then reacts DMT-Cl/Pyr reacted with the unprotected product compound, which results in the addition of DMT to the 5'—O position of ribofuranose; then reacts TBDMS-Cl, AgNO₃, and Pyr/THF with the 5'—O-DMT substituted ribofuranose; and finally performs standard phosphitylation to produce the phosphorus-containing group located at the 3'—O. Each of the syntheses presented include at least 4 to 7 steps.

Chu et al. described prodrugs that are azide derivative compounds and compositions, including nucleoside and phosphorylated nucleoside analogues (U.S. Pat. No. 6,271,212). Such azide prodrugs have as advantages their ability to cross the blood-brain barrier, provide a longer half-life, and afford greater bioavailabilty and increased stability of the active form of the drug than previously observed. However, Chu et al. reported a lengthy, multi-step synthesis required for preparing their azide prodrugs.

Borretzen et al. described antiviral prodrugs that were nucleosides and nucleoside analogues. They reported certain fatty acid esters of anti-viral nucleosides and nucleoside analogues where the fatty acid in a mono-unsaturated $C_{18}$ or $C_{20}$ fatty acid was bonded to the 5'-position of the nucleoside or nucleoside analogue through an acylation process (U.S. Pat. No. 6,153,594). The process was carried out in the presence of a catalyst, and was allowed to proceed for 24-60 hours. Product isolation was accomplished by extraction with an organic solvent, and purification by chromatography and/or recrystallization from an appropriate solvent. Percent yield of the product varied widely from 15-82%. Borretzen et al., however, did not use the term "prodrug".

In 1999, McCormick et al. described the carbonate formation at the 3'—OH of guanosine, using an unprotected ribose as a starting material (McCormick et al., *J. Am. Chem. Soc.* 1999, 121(24):5661-5). McCormick was able to synthesize the compound by a sequential, stepwise introduction of the O— and N-glycosidic linkages, application of certain protecting groups, sulfonation and final deprotection. As one step in their process, McCormick et al. reacted unprotected guanosine with BOC-anhydride, DMAP, $Et_3N$, and DMSO at room temperature for 4 hours to obtain directly a carbonate at the 3'—OH of guanosine.

Also in 1999, Tang et al. disclosed a process for preparing phosphoramidite prodrugs of 2'-C-β-methyl-cytidine ribonucleosides (Tang et al., *J. Org. Chem.*, 1999, 64:747-754). Like many of their colleagues, Tang et al. reacted 1,2,3,5-tetra-O-benzoyl-2-C-methyl-β-D ribofuranose with persilylated 4-N-benzoylcytosine in the presence of the Lewis acid, $SnCl_4$, as a first step in their synthesis (Id. at 748, Scheme 1$^a$).

In 2000, Novirio Pharmaceuticals (now Idenix) discovered that the stability and bioavailability of antiviral nucleoside analogues is enhanced by the administration of amino acid ester forms of antiviral nucleosides (U.S. Ser. No. 09/864,078, pending; U.S. Ser. No. 10/261,327, pending; WO 01/90121; and U.S. Provisional Applications Nos. 60/377,983 and 60/392,351). Processes used for preparing these amino acid esters of nucleosides and nucleoside analogues began with appropriately branched β-D or β-L nucleosides that optionally could be protected by an appropriate protecting group such as, for example, a silyl group, and subsequently deprotected, by methods known to those skilled in the art (Zhang et al., *Tetrahedron Letters*, 1992, 33:1177-80; Greene et al., *Protective Groups in Organic Synthesis*, John Wiley & Sons, 2$^{nd}$ Edition (1991); Kerr et al., *J. Pharmaceutical Sciences*, 1994, 83:582-6; Tang et al., *J. Org. Chem.*, 1999, 64(3): 747-754; and Cavelier et al., *Tetrahedron Letters*, 1996, 37:5131-4). The optionally protected branched nucleoside was then coupled with a suitable acyl donor, such as an acyl chloride and/or an acyl anhydride or an activated acid, in an appropriate protic or aprotic solvent and at a suitable reaction temperature, to provide the 2' or 3' prodrug of a 1', 2', 3' or 4' branched β-D or β-L nucleoside, optionally in the presence of a suitable coupling agent (see *Synthetic Communications*, 1978, 8(5): 327-33; *J. Am. Chem. Soc.*, 1999, 121(24):5661-5; Bryant et al., *Antimicrob. Agents Chemother.*, 2001, 45, 229-235; Standring et al., *Antiviral Chem. & Chemother.*, 2001, 12 (*Suppl.* 1), 119-129; Benzaria et al., *Antiviral Res.*, 2001, 50, A79; Pierra et al., *Antiviral Res.*, 2001, 50, A79; and Cretton-Scott et al., *Antiviral Res.*, 2001, 50, A44). Possible coupling reagents are any reagents that enable compounds or moieties to be linked to one another including, but not limited to, various carbodiimides, CDI, BOP and carbonyldiimidazole. For example, for a 3'-prodrug of a 2'-branched nucleoside, the nucleoside preferably was not protected, but was coupled directly to an alkanoic or amino acid residue via a carbodiimide-coupling reagent.

Therefore, there is a need to develop a scalable process for the commercial synthesis of activated forms of 2-deoxyribose which has in its 1 position a good leaving group that will maintain its chiral identity, during the course of the coupling reaction and upon storage.

Also, there is a need to provide a synthesis of β-L-2'-deoxynucleosides, such as β-L-thymidine, β-L-2'-deoxyuridine, and β-L-2'-deoxycytidine, and their derivatives, such as the 3'—O-acyl or 3',5'—O-diacyl prodrugs, including the 3'—O-L-aminoacyl and 3',5'—O-L-diaminoacyl prodrugs, and particularly the 3'—O-L-valinyl and 3',5'—O-L-divalinyl prodrugs.

Further, there is a need to provide a synthesis to obtain β-L-2'-deoxycytidine and its derivatives, such as its 3'—O-acyl or 3',5'—O-diacyl prodrugs, including the 3'—O-L-aminoacyl and 3',5'—O-L-diaminoacyl prodrugs, and particularly the 3'—O-L-valinyl and 3',5'—O-L-divalinyl prodrugs, under mild conditions.

In addition, there is a need to provide a more efficient synthesis to obtain β-L-2'-deoxycytidine and its derivatives, such as its 3'—O-acyl or 3',5'—O-diacyl prodrugs, including the 3'—O-L-aminoacyl and 3',5'—O-L-diaminoacyl prodrugs, and particularly the 3'—O-L-valinyl and 3',5'—O-L-divalinyl prodrugs.

Further, there is a need to provide a synthesis to obtain β-L-2'-deoxycytidine and its derivatives, such as its 3'—O-acyl or 3',5'—O-diacyl prodrugs, including the 3'—O-L-aminoacyl and 3',5'—O-L-diaminoacyl prodrugs, and particularly the 3'—O-L-valinyl and 3',5'—O-L-divalinyl prodrugs, from β-L-2'-deoxyuridine under mild conditions.

SUMMARY OF THE INVENTION

The present invention is directed to an efficient synthetic route to an optionally protected 1-halo-2-deoxyribose, preferably formed in such a condition that it can be stored and/or shipped.

This process includes formation of an alkyl acetal, such as a methyl acetal, of a furanose, such as 2-deoxyribose, optionally followed by protection of the remaining hydroxyl groups, for example in the form of aromatic esters. The optionally protected acetal is then converted under mild conditions to a 1-halo-furanose, such as a 1-halo-2-deoxyribose (halo sugar). The conditions involve the use of anhydrous acid halide, such as HCl, produced in situ by the reaction of an acyl halide, such as an acyl chloride, and in particular acetyl chloride, with sub-equivalent amounts of an alcohol, such as methanol. In a preferred embodiment, the substitute reaction is accomplished under anhydrous. conditions. In one embodiment, under the conditions of the reaction, the stereoselective substitution of the alkyoxyl group, such as a methoxyl group, for halide, such as chloride, is complete.

In one embodiment, the product crystallizes readily as it forms, thus avoiding the usual decomposition observed with other methods.

In a particular subembodiment, 2-deoxyribose is reacted with methanol to form the 1-methyl acetal of 2-deoxyribose, followed by protection of the 3- and 5-hydroxyl groups in the form of aromatic esters. The protected acetal is then converted under mild conditions to the 1-chloro-2-deoxyribose derivative (chloro sugar). The conditions involve the use of anhydrous HCl produced in situ by the reaction of an acetyl chloride with sub equivalent amounts of methanol. Preferably, the substitute reaction is accomplished under anhydrous conditions. Under the conditions of the reaction, the stereoselective substitution of the methoxyl group for chloride is complete. The product crystallizes readily as it forms, thus avoiding the usual decomposition observed with other methods. The yields are usually high (such as greater than 80% from 2-deoxyribose), the product is stable and usually has a very high content of the active intermediate (for example greater than 97%, as evaluated by a HPLC procedure or an argentometric method).

A preferred embodiment of the halo sugar production process includes a series of steps to convert the 1-hydroxyl group of 2-deoxyribose to a halo group. According to this synthesis, the starting material 2-deoxyribose (a hemiacetal) is first transformed to 1—O-alkyl-2-deoxyribose (an acetal) through acid catalyzed alcoholic conversion of the hemiacetal group to the acetal or 2'-deoxy ribose alkyl glycoside. In one embodiment, the alkyl group of the alkyl glycoside is methyl or ethyl, preferably methyl. The hydroxyls of the 2-deoxyribose alkyl glycoside are then optionally protected by conversion to esters. The alkyl glycoside is reacted with an aromatic acid halide and acid scavenger to form the 3,5-di-O-diarylacyl-2-deoxyribose alkyl glycoside. A preferred arylacyl group is a toluoyl group corresponding to the aromatic acid toluic acid. The remaining step of the halo sugar production involves a substitution reaction of the alkoxy acetal group. According to the invention, the alkoxy group of the 3,5—O-diarylacyl-2-deoxyribose alkyl glycoside undergoes a substitution reaction with halide to form the 1-halo-3,5—O-diarylacyl-2-deoxyribose, preferably under anhydrous conditions.

The coupling reaction was found to be dependent on the solvent and the ratio of silylated base to chloro-sugar. The solvent requirement can be very strict. For example, chloroform provides good yields with high stereoselectivity. An excess of silylated base promotes the formation of the β nucleoside in greater proportion. While a 1:1 ratio can lead to a β/α of ca 10-12, a molar excess, such as a 2 molar excess, of the silylated base can provide ratios as high as 40-45. When an excess of base is used, the excess base, after decomposition, is easily removed with the help of a filtering aid. Further, the α isomer is easily removed by selective crystallization, for example from 95% ethyl alcohol.

The protected pure β nucleosides thus isolated are then subjected to a sodium methoxide catalyzed trans esterification reaction in methanol. The free nucleosides are easily crystallized in almost quantitative yields. In this manner L-dT and LdU may be easily made in large quantities.

This invention also discloses an efficient synthetic route to cytidine nucleosides, such as L-2'-deoxycytidine (L-dC), from available precursors with the option of introducing functionality as needed. The process of synthesis is applicable to a wide range of derivatives of cytidine. The L-dC compounds made according to the present invention can also be used as synthetic intermediates for the preparation of a large variety of other nucleoside analogs, including, but not limited to, 2',3'-dideoxy and other derivatives obtained by subsequent functional group manipulations.

This process utilizes a sulfonyl halide, such as tosyl chloride, optionally in the presence of a phase transfer catalyst, such as a pyridinium salt, to achieve the subsequent amination, for example with gaseous or liquid ammonia, of β-(D or L)- or α-(D or L)-uridine, such as β-L-2'-deoxyuridine, to produce a β-(D or L)- or α-(D or L)-cytidine, such as a β-L-dC.

For example, in one embodiment, the amination sequence is initiated with the selective blocking of the 5'—OH, for example with BOC. The activation of the uracil moiety is achieved under very mild conditions by reacting the optionally protected derivative, for example the di-BOC derivative, with a sulfonyl halide, such as tosyl chloride, followed by addition of liquid (or gaseous) ammonia and allowing the mixture to react at room temperature. The ammonolysis is regioselective leading to mixtures of the uracil and cytosine nucleosides in a ratio of ca. 1:12.

In a further embodiment of the present invention, before the cytosine nucleoside is deprotected, the uracil nucleoside is removed. Therefore, the present invention is also directed to an efficient non-chromatographic separation of residual uridine derivatives from cytidine derivatives, wherein the substituents $R^1$ through $R^5$ may be almost any organic group. This separation process is scalable to multi-kilo preparations. The process takes advantage of the basicity of cytidine derivatives to form relatively water-soluble salts with hydrochloric acid and the selective extraction of the non basic components of the reaction mixture. In one embodiment of the invention, the recovery of the required blocked cytosine nucleoside is quantitative.

Briefly, the method for preparing β-(D or L)- or α-(D or L)-cytidine includes the following:

a) preparing or obtaining a β-(D or L)- or α-(D or L)-uridine of structure (I)

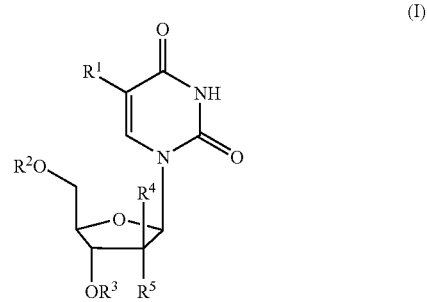

(I)

wherein $R^1$ is a hydrogen atom, an alkyl group, a substituted alkyl group, a halogen atom, an alkoxyl group or a substituted alkoxy group, wherein in certain embodiments, the alkyl groups for $R^1$ include lower alkyl groups with 1 to 6 carbon atoms such as methyl, ethyl, n-propyl, isopropyl, n-butyl and gemdimethyl butyl (i.e., 6 carbons) of all isomeric forms; the halogen includes fluorine and chlorine; the alkoxyl groups include lower alkoxyl groups with 1 to 6 carbon atoms such as methoxy, ethoxy, n-propoxy, isopropoxy and n-butoxy; and the alkyl and alkoxyl groups may be substituted with a hydroxyl group, an amino group or a halogen atom such as fluorine, chlorine, bromine, and iodine;

each $R^2$ and $R^3$ is independently hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, arylalkylsulfonyl, amino acid residue, mono, di, or triphosphate, or a phosphate derivative, wherein in certain embodiments, each of the alkyl groups may be from 1 to 6 carbons; each of the alkoxyalkyl groups may be from 2 to 10 carbons; each of the aryloxyalkyl groups may be from 7 to 15 carbons; each of the aryl groups may be from 6 to 18 carbons; each of the arylalkyl groups may be from 7 to 15 carbons; each of the amino acid residues may be any of the naturally occurring alpha amino acids and in addition, non-naturally occurring amino acids such as taurine, beta amino propionic acid or gamma amino butyric acid; and each $R^4$ and $R^5$ is independently a hydrogen atom, an alkyl group, a substituted alkyl group, a halogen atom, an alkoxyl group, a substituted alkoxyl group, or an acyloxyl group, wherein in certain embodiments, the alkyl groups referred to in the definition of $R^4$ and/or $R^5$ include lower alkyl groups with 1 to 6 carbon atoms such as methyl, ethyl, n-propyl, isopropyl, n-butyl, and gemdimethyl butyl; the halogen includes fluorine, bromine and chlorine; the alkoxyl groups include lower alkoxyl groups with 1 to 6 carbon atoms such as methoxy, ethoxy, n-propoxy, and n-epoxy; the acyloxy groups include O-carboxy aliphatic or aromatic groups, such as acetyl, benzoyl, toluoyl, p-Cl-benzoyl; and the alkyl and alkoxy groups may be substituted with a hydroxyl group, an amino group or a halogen atom such as fluorine, chlorine, bromine, and iodine; and then b) activating the compound of structure (I) with a sulfonyl halide of structure (II)

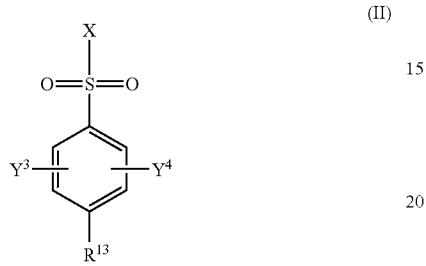

(II)

such as tosyl chloride, optionally in the presence of a phase transfer catalyst, such as a pyridinium salt of structure (III)

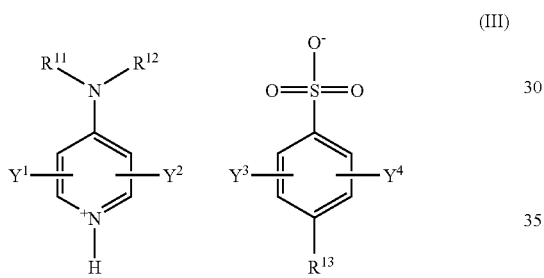

(III)

wherein
X is a halogen (F, Cl, Br, and I);
$R^{11}$, $R^{12}$ and $R^{13}$ are independently hydrogen, alkyl, alkenyl or alkynyl, though preferably a lower alkyl; and
$Y^1$, $Y^2$, $Y^3$ and $Y^4$ are independently hydrogen, halogen, alkyl, alkenyl or alkynyl, acyl, alkoxy or thioalkyl, though preferably hydrogen; and then c) reacting the activated compound with an amine, such as gaseous or liquid ammonia, to form β- or α-cytidine of structure (IV)

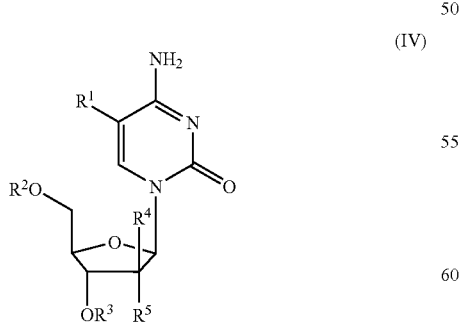

(IV)

wherein $R^1$, $R^2$, $R^3$, $R^4$, and $R^5$ are defined above.

In one embodiment, the method is directed to the preparation of a β-L-2'-deoxy-cytidine, which includes the following:

a) preparing or obtaining a β-L-2'-deoxy-uridine of structure (I*)

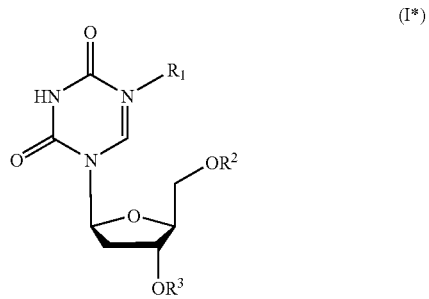

(I*)

wherein $R^2$ and $R^3$ are independently hydrogen, acyl, silyl or a derivative of an amino acid; and $R^1$ is hydrogen, halogen, alkyl, alkenyl or alkynyl, acyl, amine, alkylamine, aminoalkyl, hydroxyl, alkoxy, oxyalkyl, thiol, thioalkyl or alkylmercaptan; and then b) activating the compound of structure (I*) with a sulfonyl halide of structure (II)

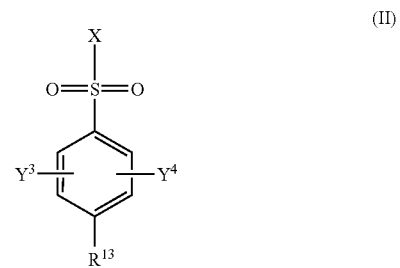

(II)

such as tosyl chloride, optionally in the presence of a phase transfer catalyst, such as a pyridinium salt of structure (III)

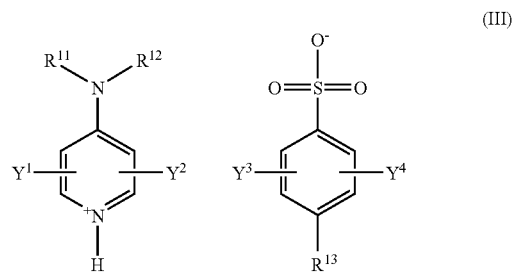

(III)

wherein
X is a halogen (F, Cl, Br, and I);
$R^{11}$, $R^{12}$ and $R^{13}$ are independently hydrogen, alkyl, alkenyl or alkynyl, though preferably a lower alkyl; and
$Y^1$, $Y^2$, $Y^3$ and $Y^4$ are independently hydrogen, halogen, alkyl, alkenyl or alkynyl, acyl, alkoxy or thioalkyl, though preferably hydrogen; and then c) reacting the activated compound with an amine, such as gaseous or liquid ammonia, to form a β-L-2'-deoxy-cytidine of structure (IV*)

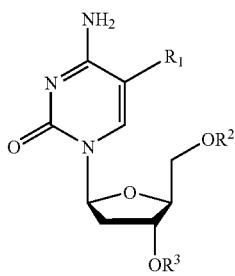

(IV*)

wherein $R^1$, $R^2$ and $R^3$ are defined above.

In one embodiment of the invention, the process further includes esterifing the nucleosides, such as 2'-deoxy-β-L-nucleosides, to obtain the corresponding 5',3', and/or 3',5'-prodrugs, such as the 5'-aminoacyl, 3'-aminoacyl, and/or 3',5'-diaminoacyl prodrugs, and in particular 5'-L-valinyl, 3'-L-valinyl, and/or 3',5'-L-divalinyl prodrugs, and specifically 5'-L-valinyl, 3'-L-valinyl, and/or 3',5'-L-divalinyl prodrugs of L-dT and L-dC.

Briefly, this additional process steps includes the following steps:

a) preparing or obtaining a β-L or D-nucleoside of the following formula (V):

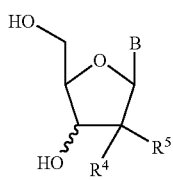

(V)

wherein

B is a pyrimidine, purine, heterocyclic or heteroaromatic base, optionally protected; and each $R^4$ and $R^5$ is independently a hydrogen atom, an alkyl group, a substituted alkyl group, a halogen atom, an alkoxyl group, a substituted alkoxyl group, or an acyloxyl group, wherein in certain embodiments, the alkyl groups referred to in the definition of $R^4$ and/or $R^5$ include lower alkyl groups with 1 to 6 carbon atoms such as methyl, ethyl, n-propyl, isopropyl, n-butyl, and gem-dimethyl butyl; the halogen includes fluorine, bromine and chlorine; the alkoxyl groups include lower alkoxyl groups with 1 to 6 carbon atoms such as methoxy, ethoxy, n-propoxy, and n-epoxy; the acyloxy groups include O-carboxy aliphatic or aromatic groups, such as acetyl, benzoyl, toluoyl, p-Cl-benzoyl; and the alkyl and alkoxy groups may be substituted with a hydroxyl group, an amino group or a halogen atom such as fluorine, chlorine, bromine, and iodine; and then b) obtaining an aminoacyl derivative of the following formula (VI):

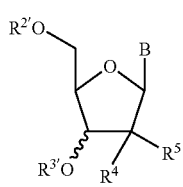

(VI)

wherein $R^{2'}$ and $R^{3'}$ are independently hydrogen, acyl, silyl or a derivative of an amino acid; and at least one of $R^{2'}$ and $R^{3'}$ are a derivative of an amino acid.

Therefore, in one embodiment, this additional process steps includes the following steps:

a) preparing or obtaining a β-L-2'-deoxynucleoside of the following formula (V*):

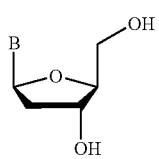

(V*)

wherein B is a pyrimidine, purine, heterocyclic or heteroaromatic base, optionally protected;

b) preparing an aminoacyl derivative of the following formula (VI*):

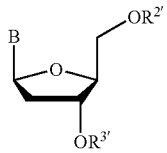

(VI*)

wherein $R^{2'}$ and $R^{3'}$ are independently hydrogen, acyl, silyl or a derivative of an amino acid; and at least one of $R^{2'}$ and $R^{3'}$ are a derivative of an amino acid.

In one embodiment of the invention, only the 3'-hydroxyl is esterified. In one such embodiment, introduction of the acyl moiety, such as a valyl moiety, at 3'-hydroxyl is accomplished by preliminary selective blocking of 5'—OH. This is easily achieved with the use of trityl chloride under controlled conditions. The intermediate thus formed is selectively de-tritylated under conditions that keep the t-butyl-oxy-carbonyl (BOC) protecting group of the valyl moiety intact. The intermediate produced is 3'-O-BOC-L-valyl-L-dU a crystalline and stable intermediate.

In one embodiment, the present invention includes a process for the synthesis of 3'-prodrugs or 3',5'-prodrugs of L-dC, for example 3'—O-acyl or 3',5'-diacyl prodrugs of L-dC, such as 3'—O-aminoacyl or 3',5'—O-diaminoacyl prodrugs of LdC, and in particular 3'—O-L-valinyl or 3',5'—O-L-divalinyl prodrugs of L-dC, wherein the 3' and/or 5'-hydroxyl is esterified prior to animation of the optionally protected 2'-deoxyuridine. In an alternative embodiment, the invention is directed to a process of the synthesis of 3'-prodrugs or 3',5'-prodrugs of L-dC, for example 3'—O-acyl or 3',5'-diacyl prodrugs of L-dC, such as 3'—O-aminoacyl or 3',5'—O-diaminoacyl prodrugs of LdC, and in particular 3'—O-L-valinyl or 3',5'—O-L-divalinyl prodrugs of L-dC, wherein the 3' and/or 5'-hydroxyl is esterified to the desired bio-labile substituent subsequent to the amination of the optionally protected 2'-deoxyuridine.

As a non-limiting example, the synthesis can follow the following scheme:

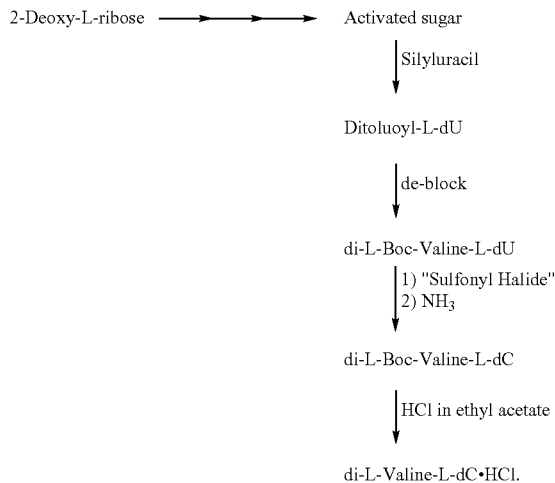

In addition to describing very efficient and scalable syntheses for 1-α-chloro-3,5-di-O-p-toluoyl-2-deoxy-L-ribose, LdT, LdU, 3'—O-L-val-LdC, and 3',5'—O-L-dival-L-dC, the present invention also reveals five compounds that constitute intermediates in the synthetic routes to final cytidine compounds. These compounds include:

5'—O-Trityl-2'-deoxy-β-L-uridine and pharmaceutically acceptable salts or isomers thereof;

3'—O—N-Boc-L-valyl-5'—O-Trityl-2'-deoxy-β-L-uridine and pharmaceutically acceptable salts or isomers thereof;

3'—O—N-Boc-L-valyl-2'-deoxy-β-L-uridine and pharmaceutically acceptable salts or isomers thereof;

3'—O—N-Boc-L-valyl-5'—O-Boc-2'-deoxy-β-L-uridine and pharmaceutically acceptable salts or isomers thereof; and 3'—O—N-Boc-L-valyl-5'—O-Boc-2'-deoxy-β-L-cytidine and pharmaceutically acceptable salts or isomers thereof.

The pharmaceutically acceptable salts and optical isomers of these compounds are also included in the invention. These compounds are described in greater detail below.

The advantages of the processes of this invention include at least the following highlights:

1. The invention of a mild and robust procedure to produce large quantities of a stable activated 2-deoxy-sugar capable of giving highly stereoselective coupling reactions that lead to β 2'-deoxy-nucleosides.
2. A mild and selective de-tritylation procedure performed in the presence of a N—BOC protected amino-acyl group.
3. A selective extraction procedure that allows the isolation of pure cytosine aminoacyl nucleosides, thus avoiding unaffordable chromatographic procedures.
4. The concept of using BOC to protect the aminoacyl moiety and the 5'—OH, which allows the simultaneous de-protection of both sites without the formation of difficult to eliminate side products as well as the formation of the desired crystalline di-hydrochloride.

DETAILED DESCRIPTION OF THE FIGURES

FIG. 1 is a non-limiting illustrative example according to the present invention of the synthesis of 4-(N,N-dimethylamino)pyridinium 4-toluenesulfonate from DMAP and TsOH.

FIG. 2 is a non-limiting illustrative example according to the present invention of the synthesis of 3',5'-di-(N-Boc-L-valinyl)-2'-deoxy-β-L-cytidine from 3',5'-di-(N-Boc-L-valinyl)-2'-deoxy-β-L-uridine.

FIG. 3 is an illustrative scheme according to the present invention depicting the conversion of 2'-deoxyribose to 1'-chloro-2'-deoxyribose and the coupling of this compound with a silyled thymine to give, after deprotection, β-L-thymine.

FIG. 4 is a non-limiting illustrative scheme according to the present invention, depicting the conversion of L-dU to Val-L-dC dihydrochloride.

DETAILED DESCRIPTION OF THE INVENTION

The present invention is directed to an efficient synthetic route to an optionally protected 1-halo-2-deoxyribose, preferably formed in such a condition that it can be stored and/or shipped.

This process includes formation of an alkyl acetal, such as a methyl acetal, of a furanose, such as 2-deoxyribose, optionally followed by protection of the remaining hydroxyl groups, for example in the form of aromatic esters. The optionally protected acetal is then converted under mild conditions to a 1-halo-furanose, such as a 1-halo-2-deoxyribose (halo sugar). The conditions involve the use of anhydrous acid halide, such as HCl, produced in situ by the reaction of an acyl halide, such as an acyl chloride, an in particular acetyl chloride, with sub-equivalent amounts of an alcohol, such as methanol. In a preferred embodiment, the substitute reaction is accomplished under anhydrous conditions. In one embodiment, under the conditions of the reaction, the stereoselective substitution of the alkyoxyl group, such as a methoxyl group, for halide, such as chloride, is complete.

In one embodiment, the product crystallizes readily as it forms, thus avoiding the usual decomposition observed with other methods.

In a particular subembodiment, 2-deoxyribose is reacted with methanol to form the 1-methyl acetal of 2-deoxyribose, followed by protection of the 3- and 5-hydroxyl groups in the form of aromatic esters. The protected acetal is then converted under mild conditions to the 1-chloro-2-deoxyribose derivative (chloro sugar). The conditions involve the use of anhydrous HCl produced in situ by the reaction of an acetyl chloride with sub equivalent amounts of methanol. Preferably, the substitute reaction is accomplished under anhydrous conditions. Under the conditions of the reaction, the stereoselective substitution of the methoxyl group for chloride is complete. The product crystallizes readily as it forms, thus avoiding the usual decomposition observed with other methods. The yields are usually high (such as greater than 80% from 2-deoxyribose), the product is stable and usually has a very high content of the active intermediate (such as greater than 97%, as evaluated by a HPLC procedure or an argentometric method).

A preferred embodiment of the halo sugar production process includes a series of steps to convert the 1-hydroxyl group of 2-deoxyribose to a halo group. According to this synthesis, the starting material 2-deoxyribose (a hemiacetal) is first transformed to 1—O-alkyl-2-deoxyribose (an acetal) through acid catalyzed alcoholic conversion of the hemiacetal group to the acetal or 2'-deoxy ribose alkyl glycoside. In one embodiment, the alkyl group of the alkyl glycoside is methyl or ethyl, preferably methyl. The hydroxyls of the 2-deoxyribose alkyl glycoside are then optionally protected by conversion to esters. The alkyl glycoside is reacted with an aromatic acid halide and acid scavenger to form the 3,5-di-O-diarylacyl-2-deoxyribose alkyl glycoside. A preferred arylacyl group is a toluoyl group corresponding to the aromatic acid toluic acid. The remaining step of the halo sugar production involves a substitution reaction of the alkoxy acetal group. According to the invention, the alkoxy-group of the 3,5—O-diarylacyl-2-deoxyribose alkyl glycoside undergoes a substitution reaction with halide to form the 1-halo-3,5—O-diarylacyl-2-deoxyribose, preferably under anhydrous conditions.

The coupling reaction was found to be dependent on the solvent and the ratio of silylated base to chloro-sugar. The solvent requirement can be strict. For example, chloroform provides good yields with high stereoselectivity. An excess of silylated base promotes the formation of the β nucleoside in greater proportion. While a 1:1 ratio can lead to a β/α of ca 10-12, a molar excess, such as a 2 molar excess, of the silylated base can provide ratios as high as 40-45. When an excess of base is used, the excess base, after decomposition, is easily removed with the help of a filtering aid. Further, the α isomer is easily removed by selective crystallization, for example from 95% ethyl alcohol.

The protected pure β nucleosides thus isolated are then subjected to a sodium methoxide catalyzed trans esterification reaction in methanol. The free nucleosides are easily crystallized in almost quantitative yields. In this manner L-dT and LdU may be easily made in large quantities.

This invention also discloses an efficient synthetic route to cytidine nucleosides, such as L-2'-deoxycytidine (L-dC), from available precursors with the option of introducing functionality as needed. The process of synthesis is applicable to a wide range of derivatives of cytidine. The L-dC compounds made according to the present invention can also be used as synthetic intermediates for the preparation of a large variety of other nucleoside analogs, including, but not limited to, 2',3'-dideoxy and other derivatives obtained by subsequent functional group manipulations.

This process utilizes a sulfonyl halide, such as tosyl chloride, optionally in the presence of a phase transfer catalyst, such as a pyridinium salt, to achieve the subsequent amination, for example with gaseous or liquid ammonia, of β-(D or L)- or α-(D or L)-uridine, such as β-L-2'-deoxyuridine, to produce a β-(D or L)- or α-(D or L)-cytidine, such as a β-L-dC.

For example, in one embodiment, the amination sequence is initiated with the selective blocking of the 5'—OH, for example with BOC. The activation of the uracil moiety is achieved under very mild conditions by reacting the optionally protected derivative, for example the di-BOC derivative, with a sulfonyl halide, such as tosyl chloride, followed by addition of liquid (or gaseous) ammonia and allowing the mixture to react at room temperature. The ammonolysis is regioselective leading to mixtures of the uracil and cytosine nucleosides in a ratio of ca. 1:12.

In further embodiment of the present invention, before the cytosine nucleoside is deprotected, the uracil nucleoside is removed. Therefore, the present invention is also directed to an efficient non-chromatographic separation of residual uridine derivatives from cytidine derivatives, wherein the substituents $R^1$ through $R^5$ may be almost any organic group. This separation process is scalable to multi-kilo preparations. The process takes advantage of the basicity of cytidine derivatives to form relatively water-soluble salts with hydrochloric acid and the selective extraction of the non basic components of the reaction mixture. In one embodiment of the invention, the recovery of the required blocked cytosine nucleoside is quantitative.

Briefly, the method for preparing β-(D or L)- or α-(D or L)-cytidine includes the following:

a) preparing or obtaining a β-(D or L)- or α-(D or L)-uridine of structure (I)

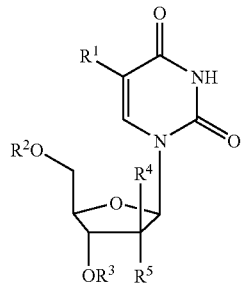

(I)

wherein $R^1$ is a hydrogen atom, an alkyl group, a substituted alkyl group, a halogen atom, an alkoxyl group or a substituted alkoxy group, wherein in certain embodiments, the alkyl groups for $R^1$ include lower alkyl groups with 1 to 6 carbon atoms such as methyl, ethyl, n-propyl, isopropyl, n-butyl and gemdimethyl butyl (i.e., 6 carbons) of all isomeric forms; the halogen includes fluorine and chlorine; the alkoxyl groups include lower alkoxyl groups with 1 to 6 carbon atoms such as methoxy, ethoxy, n-propoxy, isopropoxy and n-butoxy; and the alkyl and alkoxyl groups may be substituted with a hydroxyl group, an amino group or a halogen atom such as fluorine, chlorine, bromine, and iodine;

each $R^2$ and $R^3$ is independently hydrogen, straight chained, branched or cyclic alkyl, CO-alkyl, CO-aryl, CO-alkoxyalkyl, CO-aryloxyalkyl, CO-substituted aryl, alkylsulfonyl, arylsulfonyl, arylalkylsulfonyl, amino acid residue, mono, di, or triphosphate, or a phosphate derivative, wherein in certain embodiments, each of the alkyl groups may be from 1 to 6 carbons; each of the alkoxyalkyl groups may be from 2 to 10 carbons; each of the aryloxyalkyl groups may be from 7 to 15 carbons; each of the aryl groups may be from 6 to 18 carbons; each of the arylalkyl groups may be from 7 to 15 carbons; each of the amino acid residues may be any of the naturally occurring alpha amino acids and in addition, non-naturally occurring amino acids such as taurine, beta amino propionic acid or gamma amino butyric acid; and each $R^4$ and $R^5$ is independently a hydrogen atom, an alkyl group, a substituted alkyl group, a halogen atom, an alkoxyl group, a substituted alkoxyl group, or an acyloxyl group, wherein in certain embodiments, the alkyl groups referred to in the definition of $R^4$ and/or $R^5$ include lower alkyl groups with 1 to 6 carbon atoms such as methyl, ethyl, n-propyl, isopropyl, n-butyl, and gem-dimethyl butyl; the halogen includes fluorine, bromine and chlorine; the alkoxyl groups include lower alkoxyl groups with 1 to 6 carbon atoms such as methoxy, ethoxy, n-propoxy, and n-epoxy; the acyloxy groups include O-carboxy aliphatic or aromatic groups, such as acetyl, benzoyl, toluoyl, p-Cl-benzoyl; and the alkyl and alkoxy groups may be substituted with a hydroxyl group, an amino group or a halogen atom such as fluorine, chlorine, bromine, and iodine; and then b) activating the compound of structure (I) with a sulfonyl halide of structure (II)

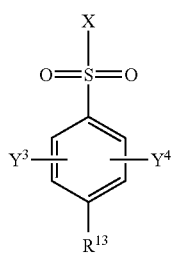

(II)

such as tosyl chloride, optionally in the presence of a phase transfer catalyst, such as a pyridinium salt of structure (III)

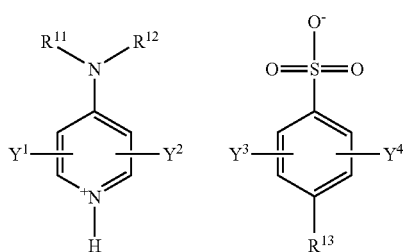

(III)

wherein
X is a halogen (F, Cl, Br, and I);
$R^{11}$, $R^{12}$ and $R^{13}$ are independently hydrogen, alkyl, alkenyl or alkynyl, though preferably a lower alkyl; and
$Y^1$, $Y^2$, $Y^3$ and $Y^4$ are independently hydrogen, halogen, alkyl, alkenyl or alkynyl, acyl, alkoxy or thioalkyl, though preferably hydrogen; and then c) reacting the activated compound with an amine, such as gaseous or liquid ammonia, to form a β- or α-cytidine of structure (IV)

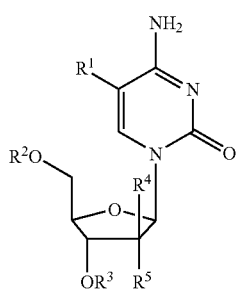

(IV)

wherein $R^1$, $R^2$, $R^3$, $R^4$, and $R^5$ are defined above.

Optionally, any of the groups of $R^1$-$R^5$ (e.g., alkyl alkoxy, cyclic alkyl and aromatic groups) can independently be substituted. Preferred embodiments for the uracil nucleoside of formula I include those wherein $R^1$, $R^4$, and $R^5$ are H; wherein R is a methyl group, and $R^4$, and $R^5$ are H; wherein $R^2$ is an amino acid residue, and especially L-valyl; and wherein $R^2$ and $R^3$ independently are each an amino acid residue, especially L-valyl.

In one embodiment, the method is directed to the preparation of a β-L-2'-deoxy-cytidine, which includes the following:

a) preparing or obtaining a β-L-2'-deoxy-uridine of structure (I*)

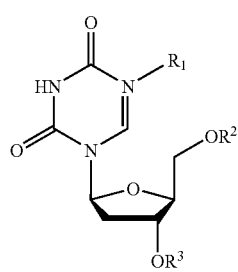

(I*)

wherein $R^2$ and $R^3$ are independently hydrogen, acyl, silyl or a derivative of an amino acid; and
$R^1$ is hydrogen, halogen, alkyl, alkenyl or alkynyl, acyl, amine, alkylamine, aminoalkyl, hydroxyl, alkoxy, oxyalkyl, thiol, thioalkyl or alkylmercaptan; and then b) activating the compound of structure (I*) with a sulfonyl halide of structure (II)

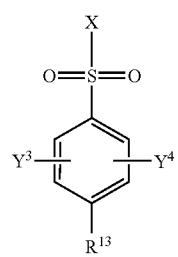

(II)

such as tosyl chloride, optionally in the presence of a phase transfer catalyst, such as a pyridinium salt of structure (III)

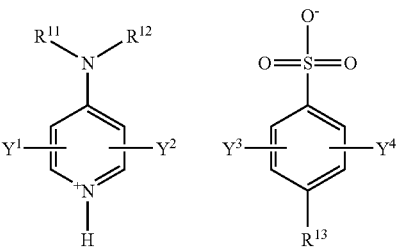

(III)

wherein
X is a halogen (F, Cl, Br, and I);
$R^{11}$, $R^{12}$ and $R^{13}$ are independently hydrogen, alkyl, alkenyl or alkynyl, though preferably a lower alkyl; and $Y^1$, $Y^2$, $Y^3$ and $Y^4$ are independently hydrogen, halogen, alkyl, alkenyl or alkynyl, acyl, alkoxy or thioalkyl, though preferably hydrogen; and then c) reacting the activated compound with an amine, such as gaseous or liquid ammonia, to form a β-L-2'-deoxycytidine of structure (IV*)

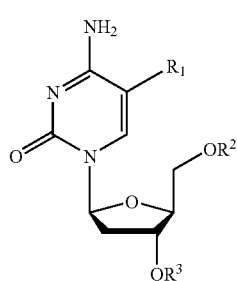

(IV*)

wherein $R^1$, $R^2$ and $R^3$ are defined above.

In one embodiment of the invention, the process further includes esterifing the nucleosides, such as 2'-deoxy-β-L-nucleosides, to obtain the corresponding 5',3', and/or 3',5'-prodrugs, such as the 5'-aminoacyl, 3'-aminoacyl, and/or 3',5'-diaminoacyl prodrugs, and in particular 5'-L-valinyl, 3'-L-valinyl, and/or 3',5'-L-divalinyl prodrugs, and specifically 5'-L-valinyl, 3'-L-valinyl, and/or 3',5'-L-divalinyl prodrugs of L-dT and L-dC.

Briefly, this additional process steps includes the following steps:

a) preparing or obtaining a β-L or D-nucleoside of the following formula (V):

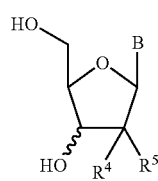

(V)

wherein

B is a pyrimidine, purine, heterocyclic or heteroaromatic base, optionally protected; and each $R^4$ and $R^5$ is independently a hydrogen atom, an alkyl group, a substituted alkyl group, a halogen atom, an alkoxyl group, a substituted alkoxyl group, or an acyloxyl group, wherein in certain embodiments, the alkyl groups referred to in the definition of $R^4$ and/or $R^5$ include lower alkyl groups with 1 to 6 carbon atoms such as methyl, ethyl, n-propyl, isopropyl, n-butyl, and gem-dimethyl butyl; the halogen includes fluorine, bromine and chlorine; the alkoxyl groups include lower alkoxyl groups with 1 to 6 carbon atoms such as methoxy, ethoxy, n-propoxy, and n-epoxy; the acyloxy groups include O-carboxy aliphatic or aromatic groups, such as acetyl, benzoyl, toluoyl, p-Cl-benzoyl; and the alkyl and alkoxy groups may be substituted with a hydroxyl group, an amino group or a halogen atom such as fluorine, chlorine, bromine, and iodine; and then b) obtaining an aminoacyl derivative of the following formula (VI):

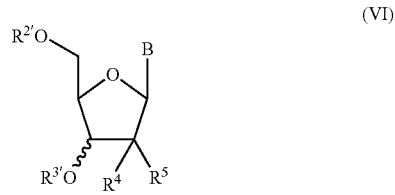

(VI)

wherein $R^{2'}$ and $R^{3'}$ are independently hydrogen, acyl, silyl or a derivative of an amino acid; and at least one of $R^{2'}$ and $R^{3'}$ are a derivative of an amino acid.

Therefore, in one embodiment, this additional process steps includes the following steps:

a) preparing or obtaining a β-L-2'-deoxynucleoside of the following formula (V*):

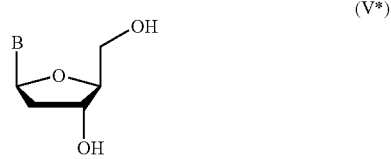

(V*)

wherein B is a pyrimidine, purine, heterocyclic or heteroaromatic base, optionally protected;

b) preparing an aminoacyl derivative of the following formula (VI*):

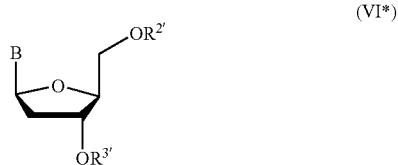

(VI*)

wherein $R^{2'}$ and $R^{3'}$ are independently hydrogen, acyl, silyl or a derivative of an amino acid; and at least one of $R^{2'}$ and $R^{3'}$ are a derivative of an amino acid.

In one embodiment of the invention, only the 3'-hydroxyl is esterified. In one such embodiment, introduction of the acyl moiety, such as a valyl moiety, at 3'-hydroxyl is accomplished by preliminary selective blocking of 5'—OH. This is easily achieved with the use of trityl chloride under controlled conditions. The intermediate thus formed is selectively de-tritylated under conditions that keep the t-butyl-oxy-carbonyl (BOC) protecting group of the valyl moiety intact. The intermediate produced is 3'—O-BOC-L-valyl-L-dU a crystalline and stable intermediate.

In one embodiment, the present invention includes a process for the synthesis of 3'-prodrugs or 3',5'-prodrugs of L-dC, for example 3'—O-acyl or 3',5'-diacyl prodrugs of L-dC, such as 3'—O-aminoacyl or 3',5'—O-diaminoacyl prodrugs of LdC, and in particular 3'—O-L-valinyl or 3',5'—O-L-divalinyl prodrugs of L-dC, wherein the 3'and/or 5'-hydroxyl is esterified prior to amination of the optionally protected 2'-deoxyuridine. In an alternative embodiment, the invention is directed to a process of the synthesis of 3'-prodrugs or 3',5'-prodrugs of L-dC, for example 3'—O-acyl or 3',5'-diacyl prodrugs of L-dC, such as 3'—O-aminoacyl or 3',5'—O-diaminoacyl prodrugs of LdC, and in particular 3'—O-L-valinyl or 3',5'—O-L-divalinyl prodrugs of L-dC, wherein the 3' and/or 5'-hydroxyl is esterified to the desired bio-labile substituent subsequent to the amination of the optionally protected 2'-deoxyuridine.

As a non-limiting example, the synthesis can follow the following scheme:

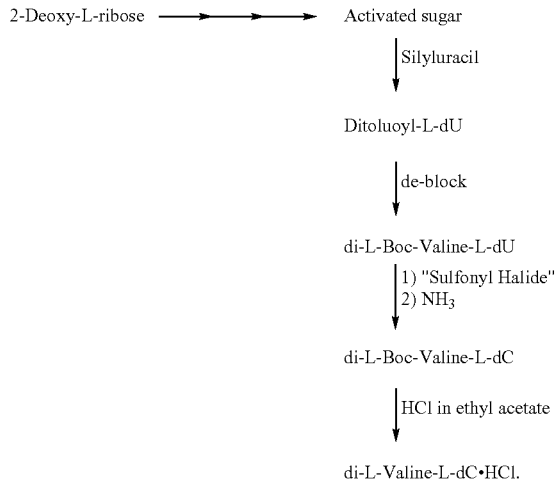

In addition to describing very efficient and scalable syntheses for 1-α-chloro-3,5-di-O-p-toluoyl-2-deoxy-L-ribose, LdT, LdU, 3'—O-L-val-LdC, and 3',5'—O-L-dival-L-dC, the present invention also reveals five compounds that constitute intermediates in the synthetic routes to final cytidine compounds. These compounds include:, 5'—O-Trityl-2'-deoxy-β-L-uridine and pharmaceutically acceptable salts or isomers thereof;

3'—O—N-Boc-L-valyl-5'—O-Trityl-2'-deoxy-β-L-uridine and pharmaceutically acceptable salts or isomers thereof;

3'—O—N-Boc-L-valyl-2'-deoxy-β-L-uridine and pharmaceutically acceptable salts or isomers thereof;

3'—O—N-Boc-L-valyl-5'—O-Boc-2'-deoxy-β-L-uridine and pharmaceutically acceptable salts or isomers thereof; and 3'—O—N-Boc-L-valyl-5'—O-Boc-2'-deoxy-β-L-cytidine and pharmaceutically acceptable salts or isomers thereof.

The pharmaceutically acceptable salts and optical isomers of these compounds are also included in the invention. These compounds are described in greater detail below.

The advantages of the processes of this invention include at least the following highlights:
1. The invention of a mild and robust procedure to produce large quantities of a stable activated 2-deoxy-sugar capable of giving highly stereoselective coupling reactions that lead to β2'-deoxy-nucleosides.
2. A mild and selective de-tritylation procedure performed in the presence of a N—BOC protected amino-acyl group.
3. A selective extraction procedure that allows the isolation of pure cytosine aminoacyl nucleosides, thus avoiding unaffordable chromatographic procedures.
4. The concept of using BOC to protect the aminoacyl moiety and the 5'—OH, which allows the simultaneous de-protection of both sites without the formation of difficult to eliminate side products as well as the formation of the desired crystalline di-hydrochloride.

The selection of reaction conditions should take into account the ease of activating the L-2'-deoxyuridine with the sulfonyl halide. Some combinations of temperature and solvent may lead to decreased yields. For example, the coupling reaction is exothermic, thus can potentially lead to side products such as anhydrides and/or ureas. Therefore, in one embodiment, to overcome these undesirable side reactions, the reaction is run at room temperature with large excess of select reagents, such as carbodiimide and valine. In an alternative embodiment, the coupling reaction is run at lower temperatures, e.g. 15±2° C., to obtain almost pure product. In addition, the solvent systems can also be critical. As a non-limiting example, when the prodrug precursor, di-L-Boc-Valine-L-dC is deprotected with HCl in dioxane, the dioxane has an increased affinity to the prodrug and cannot be completely removed from the desired product, with 5-6% of the product being dioxane. If, on the other hand, ethyl acetate is employed as the solvent, the desired product has almost no trace of solvent.

Further, if the prodrug di-aminoacid-L-dC is the desired product, the conditions set forth in U.S. Pat. No. 4,754,026 are inapplicable due to the instability of the intermediates to the release of HCl, either due to racemization of the amino acid or nucleoside, or even decomposition. Therefore, in one embodiment, when milder conditions are desired, a phase transfer catalysts is used.

If desired, the L-dC nucleoside can then be reduced to a L-2',3'-dideoxycytidine or a L-2',3'-dideoxy-2',3'-didehydro-cytidine using known methods; as a non-limiting illustrative example, Townsend, et al., *Chemistry of Nucleosides and Nucleotides, Volume* 1, Plenum Press: New York, teaches reduction of nucleosides at the 3' position to give 2',3'-dideoxynucleosides and elimination of the 3'-hydroxyl to give 2',3'-dideoxy-2',3'-didehydronucleosides. Alternatively, the 3'-position can be modified to form 3' or 5' substituted cytidine derivatives, or a combination thereof, also using known chemistry to those skilled in the art. As a non-limiting example, Kuzuhara, H., et al., U.S. Pat. No. 5,144,018 (1992) teaches functionalizing the relevant hydroxyl by activation and subsequent substitution.

Definitions

It should be understood that the various possible stereoisomers of the groups mentioned above and herein are within the meaning of the individual terms and examples, unless otherwise specified. As an illustrative example, "1-methyl-butyl" exists in both the (R) and the (S) form, thus, both (R)-1-methyl-butyl and (S)-1-methyl-butyl is covered by the term "1-methyl-butyl", unless otherwise specified. Several biological compounds are designed by the (D) and the (L) form, rather than the (R) and the (S) form, respectively, based on the stereochemistry around the 4' carbon. As an another illustrative example, "glycine" exists in both the (D) and the (L) form; therefore, both (D)-glycine and (L)-glycine are covered by the term "glycine" unless otherwise specified.

As used herein, the term "substantially free of" or "substantially in the absence of" refers to a nucleoside composition that includes at least 85 or 90% by weight, preferably 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "alkyl," as used herein, unless otherwise specified, refers to a saturated straight, branched, or cyclic, primary, secondary, or tertiary hydrocarbon, including but not limited to those of $C_1$ to $C_{16}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties such as a halo (F, Cl, Br, or I, e.g. $CH_2F$ or $CF_3$), alkyl, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms.

The term alkylene or alkenyl refers to a saturated hydrocarbyldiyl radical of straight or branched configuration, including but not limited to those that have from one to ten carbon atoms. Included within the scope of this term are methylene, 1,2-ethane-diyl, 1,1-ethane-diyl, 1,3-propane-diyl, 1,2-propane-diyl, 1,3-butane-diyl, 1,4-butane-diyl and the like. The alkylene group or other divalent moiety disclosed herein can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term aryl, as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of bromo, chloro, fluoro, iodo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term "protected" as used herein and unless otherwise defined refers to a group that is added to a heteroatom to prevent its further reaction or for other purposes. A wide variety of oxygen and nitrogen protecting groups are known to those skilled in the art of organic synthesis.

The term "halo" or "halogen," as used herein, includes chloro, bromo, iodo, and fluoro.

The term "alkoxy," as used herein, and unless otherwise specified, refers to a moiety of the structure —O-alkyl, wherein alkyl is as defined above.

The term "acyl," as used herein, refers to a group of the formula C(O)R', wherein R' is an alkyl, aryl, alkaryl or aralkyl group, or substituted alkyl, aryl, aralkyl or alkaryl, wherein these groups are as defined above.

The term heteroaromatic base, as used herein, refers to an aromatic that includes at least one sulfur, oxygen, nitrogen or phosphorus in the aromatic ring. The term heterocyclic base refers to a nonaromatic cyclic group wherein there is at least one heteroatom, such as oxygen, sulfur, nitrogen, or phosphorus in the ring. The heteroaromatic group can be optionally substituted as described above for aryl. The heterocyclic group can be optionally substituted with one or more moieties selected from the group consisting of alkyl, halo, haloalkyl, hydroxyl, carboxyl, acyl, acyloxy, amino, amido, carboxyl derivatives, alkyl amino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference. The heteroaromatic can be partially or totally hydrogenated as desired. As a nonlimiting example, dihydropyridine can be used in place of pyridine. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl.

The term pyrimidine, purine, heteroaromatic base, or heterocyclic base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, v-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolo-pyrimidinyl. Purine bases specifically include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl and t-butyldiphenylsilyl, trityl, alkyl groups, and acyl groups such as acetyl and propionyl, methanesulfonyl, and p-toluenesulfonyl. Alternatively, the pyrimidine, purine, heteroaromatic base, or heterocyclic base can optionally substituted such that it forms a viable prodrug, which can be cleaved in vivo. Examples of appropriate substituents include acyl moiety, an amine or cyclopropyl (e.g., 2-amino, 2,6-diamino or cyclopropyl guanosine).

The term amino acid includes naturally occurring and synthetic α, β γ or δ amino acids, and includes but is not limited to, alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, and β-histidinyl.

DETAILED DESCRIPTION OF THE PROCESS STEPS

1. Synthesis of the Activated Sugar (1-α-Chloro-3,5-di-O-toluoyl-2-deoxy-L-ribose)

The synthetic procedure described below enables the isolation and storage of the halo-sugar, such as a chloro-sugar, with maintenance of the chiral identity. A benefit that has heretofore not been achieved.

There are three steps for the production of the halo-sugar, such as a chloro-sugar: first is the conversion of furanose, such as 2-deoxy ribose, that is a hemiacetal, to an alkyl acetal or alkyl glycoside, such as 1—O-methyl-2-deoxy ribose; followed by the optional protection of the remaining free hydroxyls if desired, for example as ester groups (the protecting ester may be formed from an acyl group of about 3 to about 20 carbons, preferably as arylacyl group of 7 to 15 carbons, more preferably as benzoyl or substituted benzoyl groups, most preferably as toluoyl groups); third is the substitution of the alkoxy group, such as the methoxy group, with a halogen, for example a chlorine, using anhydrous acid halide, such as HCl generated in situ.

1) Alkyl Glycoside Formation

Although any alcohol, such as methanol or ethanol, can be used to form the acetal group from the hemiacetal of the furanose, such as 2-deoxy ribose, methanol is preferred. The methoxy group is a good leaving group for the subsequent halo substitution reaction. While the following description may include methanol, it is understood that another alcohol, such as ethanol, may also be used.

The conversion of the hemiacetal to the alkyl glycoside, such as methyl glycoside, is conducted under acidic conditions followed by quenching with an acid scavenger. The starting compound, such as 2-deoxyribose is combined with a stoichiometric excess of alcohol, such as methanol, and a catalytic amount of acid. Suitable catalytic acids include organic sulfonic acids such as toluene sulfonic acid and methyl sulfonic acids, and carboxylic acids, preferably organic sulfonic acids such as toluene sulfonic acid and methyl sulfonic acids. The reaction is monitored to completion and then the acid catalyst is quenched by addition of an acid scavenger. Suitable acid scavengers include any acid scavenger known in the art, including, but not limited to, triethylamine, pyridine, and dimethylaminopyridine. Isolation of the glycoside can be accomplished by removal of the excess alcohol, preferably by vacuum distillation.

The conversion of the hemiacetal to the alkyl glycoside can be carried out at any temperature that achieves the desired results, i.e., that is suitable for the reaction to proceed at an acceptable rate without promoting decomposition or excessive side products. Preferred temperatures are from room temperature to 30° C.

2) Optionally Protection of the Free Hydroxyls of the Alkyl Glycoside

The free hydroxyls of the alkyl glycoside can optionally be protected to prevent their interaction in the following halide substitution step. Protecting groups, include any suitable protecting group known in the art, including acyl and silyl groups.

The protection of the free hydroxyls can be accomplished by methods well known to those skilled in the art, as taught in Greene, et. al., *Protective Groups in Organic Synthesis*, John Wiley and Sons, Second Edition, 1991. For example, the glycoside of the previous step can be protected by an acyl group by dissolving the alkyl glycoside in an appropriate solvent and reacting the appropriate acyl halide, optionally in the presence of an acid scavenger. Suitable acid scavengers include any acid scavenger known in the art, including, but not limited to, triethylamine, pyridine, and dimethylaminopyridine.

The protection can be carried out in any solvent that is suitable for the temperature and the solubility of the reagents. Solvents can consist of any aprotic solvent including, but not limiting to, alkyl solvents such as hexane and cyclohexane, toluene, acetone, ethyl acetate, dithianes, THF, dioxane, acetonitrile, dichloromethane, dichloroethane, diethyl ether, pyridine, dimethylformamide (DMF), dimethylsulfoxide (DMSO), dimethylacetamide, or any combination thereof, though preferably ethyl acetate.

This reaction can be accomplished at any temperature that allows the reaction to proceed at an acceptable rate without promoting decomposition or excessive side products. The preferred temperature is room temperature.

The course of the reaction can be followed by appropriate identification techniques. When the reaction is complete, the acid scavenger salts can be extracted into acidic aqueous solution and the organic solution concentrated for subsequent use.

3) Production of the Halo Sugar

According to the invention, the optionally protected glycoside of step 2) can be converted to the halo sugar, preferably the chloro sugar, by exposing the protected alkyl glycoside to a substitution reaction. To perform this conversion, the organic solution of protected glycoside can be combined with a stoichometric excess of an acyl halide followed by addition of the alcohol.

The halo sugar can be prepared in any solvent that is suitable for the temperature and the solubility of the reagents. Solvents can consist of any aprotic solvent including, but not limiting to, alkyl solvents such as hexane and cyclohexane, toluene, acetone, ethyl acetate, dithianes, THF, dioxane, acetonitrile, dichloromethane, dichloroethane, diethyl ether, pyridine, dimethylformamide (DMF), dimethylsulfoxide (DMSO), dimethylacetamide, or any combination thereof, though preferably neat. Preferably, this conversion is accomplished by combining the protected glycoside in a non polar, aprotic solvent such as ether or pet ether.

The glycal can be formed at any temperature that is suitable for the reaction to proceed at an acceptable rate without promoting decomposition or excessive side products, preferably temperatures below room temperature, such as 10° C.

In one embodiment, the product crystallizes as it forms. The crystalline halo-sugar is then filtered, washed with solvent, such as pet ether, and dried to provide the halo sugar in storable form.

2. The Coupling Reaction

The coupling reaction forms a carbon-nitrogen bond between the 1-carbon of the 1-halo-sugar, such as a 1-halo-2-deoxy ribose, and a ring nitrogen of a pyrimidine, purine, heterocyclic or heteroaromatic base. To direct the coupling of the ring nitrogen, the carbonyls and amine groups, if any, of the base can be optionally protected with any suitable protecting group known in the art. Useful protecting groups for the carbonyl group of, for example, uracil, thymine, include trimethyl silyl and triethylsilyl, t-butydimethysilyl, methyl, and other alkyl ethers. Useful protecting groups for the amine group of adenine and guanine, for example, include the trityl group, the tosylate, acyl groups such as acetyl, benzoyl, and alkoxycarbonyl groups, such as benzoyl oxy carbonal, t-butoxycarbonal, and fluroenylmethylcarbonyl.

The halo-sugar can be coupled to the pyrimidine, purine, heterocyclic or heteroaromatic base using any means known in the art, to obtain an optionally protected nucleoside.

In one embodiment of the present invention, an activated purine or pyrimidine base, preferably a silylated base, is coupled to the ring, optionally in the presence of a Lewis acid, such as tin tetrachloride, titanium tetrachloride, or trimethylsilyl triflate.

The coupling of the halo-sugar with a pyrimidine, purine, heterocyclic or heteroaromatic base, such as uracil or thymine, the base can be first combined with a silylating agent such as hexamethyldisilazane, to activate the base, for example, in the case or uracil or thymine, to silylated the amide carbonyls. The resulting activated base can then be combined with the optionally protected halo sugar described above to form the protected nucleoside. One non-limiting example of such coupling is illustrated in FIG. 3.

In one embodiment, the pyrimidine, purine, heterocyclic or heteroaromatic base, such as uracil or thymine, can be combined with a stochiometric excess of silylating agent, such as hexamethyldisilazane, optionally in the presence of a mild acidic catalyst such as ammonium sulfate, under elevated temperatures to form the silylated derivative. In one particular embodiment, the silylated derivative is combined with the halo-sugar under solvated conditions without prior isolation to form the nucleoside.

The optionally protected nucleoside can then be deprotected if necessary by any means known in the art. In one non-limiting example, if the nucleoside was protected with toluoyl groups, treatment of the protected nucleoside with mild base can remove the ditoluoyl groups and yield the deprotected nucleoside.

3. Method for the Preparation of Pyridinium Arylsulfonate

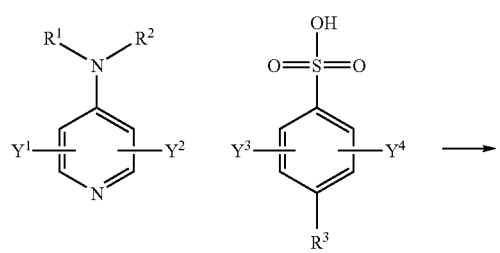

-continued

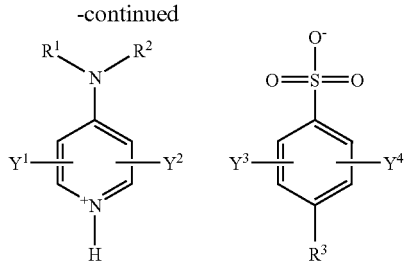

The key starting material for this process is an appropriately substituted arylsulfonic acid and pyridinium analog. The arylsulfonic acid and pyridinium base analog can be purchased or can be prepared by any known means including standard nucleophilic and electrophilic aromatic substitution. The arylsulfonic acid and pyridinium base can equilibrate to form the title compounds preferably without further catalysis.

The proton exchange reaction can be carried out at any temperature that achieves the desired results, i.e., that is suitable for the reaction to proceed at an acceptable rate without promoting decomposition or excessive side products. Preferred temperatures are from room temperature to 75° C.

Any reaction solvent can be selected that can achieve the necessary temperature and that can solubilize the reaction components, though preferably not the desired salt product. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof. The preferred solvent system is anhydrous dichloromethane followed by cyclohexane to promote in situ precipitation of the salt product.

4. Method for the Preparation of a Cytidine Nucleoside from a Uridine Nucleoside The key starting material for this process is an appropriately substituted uridine nucleoside, such as a β-L-2'-deoxyuridine. The appropriately substituted uridine nucleoside, such as β-L-2'-deoxyuridine, can be purchased or can be prepared by any known means including the procedures disclosed herein. The amination of the appropriately protected/substituted uridine nucleoside, such as an optionally protected β-L-2'-deoxyuridine, is accomplished with a sulfonyl halide, such as a tosyl halide, and in particular a tosyl chloride, optionally in the presence of a phase transfer catalyst such as a pyridinium arylsulfonate disclosed above, followed by treatment with ammonia (gaseous or liquid), affords the title compound. In one embodiment of the invention, the reaction is carried out in the presence of potassium carbonate.

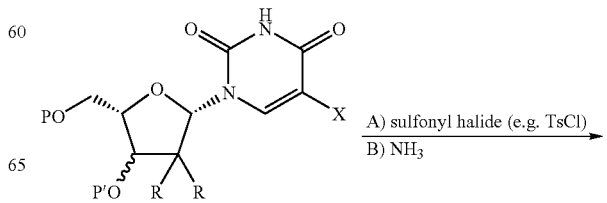

-continued

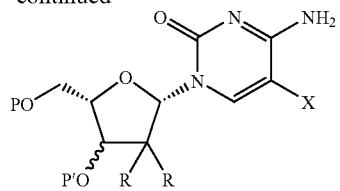

The amination reaction can be carried out at any temperature that achieves the desired results, i.e., that is suitable for the reaction to proceed at an acceptable rate without promoting decomposition or excessive side products, preferably room temperature.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane (DCM) or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof, preferably dichloromethane.

If necessary, the optionally protected cytidine nucleoside, such as an N-protected amino acid based prodrugs, can be deprotected by methods well known to those skilled in the art, as taught in Greene, et al., Protective Groups in Organic Synthesis, John Wiley and Sons, Second Edition, 1991. For example the N-Boc protected amino acids can be deprotected with HCl in ethyl acetate at room temperature.

One embodiment of the invention is directed to the process described in FIG. 4, which results in improved productivity and efficiency of each step carried out with added safety and technical convenience and resulting in elevated product purities in each step.

According to the present invention, a preferred embodiment begins with a starting uracil nucleoside optionally protected in the 5'-position of the sugar moiety, for example with a trityl derivative. After optional purification, as described below, the purified 5'—O-protected-uracil nucleoside can optionally be protected, for example aminoacylated, at the 3'-position by direct incorporation of the desired protecting group, such as an amino acyl group. This 3'-protected intermediate, for example the aminoacylated intermediate, optionally can be selectively deprotected at the 5'-position of the sugar moiety. For example, a 3'-protected intermediate that is tritylated at the 5'-position can be detritylated under mild acidic conditions, and the 3'-protected intermediate, such as an aminoacyl-uracil nucleoside, is converted to a 3'-aminoacylated cytosinylnucleoside. In one embodiment of the invention, the 5'-position of a uridine nucleoside is tritylated, followed by aminoacylation at the 3'-position, selectively deprotected at the 5'-position, and aminated to give a 3'-aminoacylated cytidine nucleoside. In another embodiment of the present invention, the conversion involves the following sequential steps: 1) O-Boc-protection of the 5'-position of a 3-aminoacylated uridine nucleoside, 2) tosylation of the uracil moiety, 3) amination of the tosylated uracil moiety to form the cytosinyl moiety, and 4) removal of the Boc-protective groups to form a 3'-aminoacyl-cytosine nucleoside.

The foregoing steps for transformation of uracil derivatives to cytosine derivatives provide a significant improvement for multi-kilogram production of high purity the cytidine derivatives for pharmaceutical use. The combination of the individual steps provides the additional advantage of minimizing waste and maximizing the efficiency of the industrial plant. In particular, the use of O-Boc protection for the 5'-hydroxyl group minimizes the number of steps and impurities in the final product. This use is especially applicable when a 3'-Boc-aminoacyl is the substituent $R^3$. Through this approach, a single deprotection step affords the desired prodrug. The selective extraction step to separate the uracil derivative from the desired cytosine derivative also conveys advantages as described above.

In a particular embodiment, the 2'-deoxycytidine nucleosides are prepared using the following steps.

Tritylation Step

The tritylation step combines the deoxyribonucleoside (2, FIG. 3), with a tritylating agent, acid scavenger and catalyst in organic solvent. This tritylation step adds a protecting group to the 5'-hydroxyl group of the 2-deoxyribose moiety but not to 3'-hydroxyl group. The tritylating agent may be a trityl or substituted trityl halide wherein the substituent may be a mono, di or tri alkyl of 1 to 3 carbons or a mono, di or tri halo group. The acid scavenger may be an organic base such as triethyl amine or pyridine. The preferred catalyst is dimethylaminopyridine (DMAP). In particular, this step can be practiced as follows. The starting deoxyribonucleoside is mixed with a dry organic solvent in the presence of an acid scavenger and a catalyst. Solvents for the reaction are chlorinated hydrocarbons, esters, and ethers, preferably dichloromethane or ethyl acetate, in amounts varying from 5 to 30 parts by volume per one part by weight of the starting nucleoside, more preferably 8, 9, 10 or 11 parts. The preferred acid scavenger is pyridine, the minimum required amount is 1 part of the starting nucleoside to promote partial solubilization of the nucleoside. The preferred catalyst is DMAP, in amounts varying from 1 to 10 mol %, more preferably 5 mol % per mole of the starting nucleoside.

The mixture is then reacted with a tritylating agent to form a 5'-protected deoxyribonucleoside product. Preferred tritylating agents are trityl chloride and substituted trityl chlorides, used in amounts varying from 1 to 1.3 moles, more preferably 1.1 moles per mole of the starting nucleoside. The tritylation reaction is preferably conducted at a temperature ranging from about 10° C. to about 40° C., more preferably from 30° C. to 35° C.

The reaction mixture can be purified by any convenient technique known to separate polar materials from nonpolar materials. For example, pyridine and other polar impurities can be removed from the nucleoside containing solution by aqueous liquid-liquid extractions. Preferred purification is performed by aqueous liquid-liquid extraction using sequential extraction of the organic reaction mixture with aqueous acid solution until substantially complete removal of pyridine, followed by extraction with aqueous sodium bicarbonate solution and water, to adjust the pH of the solution containing the protected nucleoside to 5-6;

The product can be crystallized from a mixture of organic solvents capable of retaining the non-polar impurities. Preferred organic solvents are chlorinated hydrocarbons and ketones, preferably dichloromethane and methyl isobutyl ketone (MIBK) in the ratio of 1:1. In this process, the non-polar impurities remain in solution and a high purity product is obtained.

Acylation-Detritylation Steps

The sequential acylation and detritylation steps, as depicted in FIG. 3, compound 3 to 4 and compound 4 to 5, involve acylation of the 3'hydroxyl group of the 2-deoxyribose moiety and removal of the protecting group from the 5' hydroxyl. The acyl group may be derived from any pharmaceutically acceptable carboxylic acid, any naturally occurring alpha-amino acid or any non-natural pharmaceutically acceptable amino acid as described above. The acyl group (including the aminoacyl group) provides a prodrug character to the final product. The acylation may be conducted according to any esterification technique for esterifying an acid or amino acid with an alcohol. In the case of an amino acid, its amino group will be protected with BOC.

A preferred example of this step involves reacting a mixture of a 5'-trityl-deoxyribonucleoside and a carboxylic acid in a dry organic solvent, in the presence of a catalyst, with a solution of the carbodiimide in the same organic solvent at low temperatures (10-14° C.). In one embodiment the carboxylic acid is an N-protected amino acid, preferably Boc-L-valine, in amounts varying from 1 to 1.3 moles of the starting nucleoside, preferably 1.1 moles. Preferred solvents for the reaction are chlorinated hydrocarbons, esters or ethers, preferably dichloromethane and/or ethyl acetate, in amounts varying from 5 to 15 parts by volume per one part by weight of the starting nucleoside, more preferably 6, 7, or 8 parts. Preferred catalysts are substituted pyridines, preferably DMAP, in amounts varying from 1 to 10 mol %, more preferably up to 5 mol % per mole of the starting nucleoside. Preferred carbodiimide is DCC in amounts varying from 1 to 1.5 moles of the starting nucleoside, preferably 1.2 moles.

The acylated intermediate is separated from the reaction mixture by filtering the neutral urea by-product and extracting the nucleoside containing solution to remove the polar impurities. Preferred purification is performed by aqueous liquid-liquid extraction using sequential extraction of the organic reaction mixture with aqueous acid solution to remove DMAP, followed by extraction with aqueous sodium bicarbonate solution to adjust the pH of the organic phase to 5-6 and finally with brine. Additional filtration to remove DCU may be necessary; following partial distillation of the reaction solvent.

Detritylation is accomplished by acid catalyzed thiol exchange. For example, the partially distilled solution of the aminoacylated trityl-nucleoside is reacted with a thiol in the presence of an acid catalyst at temperatures in the range of 20 to 40° C., preferably 28-32° C. Preferred thiols are mercaptoethanol and ethanethiol in amounts varying from 1 to 1.3 moles per mole of the starting nucleoside, preferably 1.1 moles. A preferred catalyst is p-toluenesulfonic acid, in amounts varying from 1 to 10 mol %, more preferably 7-8 mol % per mole of the starting nucleoside. The reaction is quenched with an amine, preferably triethylamine in amounts varying from 1 to 10 mol %, more preferably 7-8 mol % per mole of the starting nucleoside. The reaction mixture is extracted with brine to remove the amine salt. The acylated intermediate is crystallized from a mixture of organic solvents capable of retaining majority of the non-polar impurities after distilling the reaction solvent. Preferred organic solvents are hydrocarbons and aromatic hydrocarbons, preferably xylene and hexanes in the ratio of 1:1, in amounts varying from 2 to 4 parts by volume per one part by weight of the starting nucleoside. The non-polar impurities are removed by treating the product several times (typically 3 to 5 times) with the same solvent mixture used above until the non-polar impurities are removed from the protected nucleoside.

Boc-Protection-Tosylation-Amination-Deprotection Steps.

The present invention is based at least in part upon the discovery that carrying out a sequential Boc protection of the 5' hydroxyl, tosylation at C-4 in the uracil moiety and its conversion to an amino group can be carried out without isolation of intermediates, or in other words, can be carried out in an uninterrupted fashion. For efficient, high yield, the Boc-protected uracylnucleoside is to be used as soon as the reaction is complete. The reaction can be followed by any convenient identification technique such as high performance liquid chromatography (HPLC), thin layer chromatography (TLC) and the like to determine reaction end point. Immediately following the end point, the reactants of the tosylation reaction are incorporated into the reaction mixture. Preferably, the Boc protected intermediate is not allowed to stand in a completed form for longer than 3, more preferably 1 hour. Additionally, the potassium carbonate base is in the sesquihydrate form and is to be freshly prepared so that the tosylation reaction will be rapidly completed upon the addition of the tosylating agent. It has been found that, especially for multi-kilogram preparations, use of stale potassium carbonate sesquihydrate produces a very slow reaction, results in decomposition of the reactive intermediates and necessitates additional incorporation of reagents. It was discovered that the sesquihydrate form of potassium carbonate allows the tosylation reaction to proceed at low temperatures, which is desirable especially in the presence of aminoacyl groups to avoid racemization.

Upon completion of the tosylation reaction, the reaction mixture is filtered under inert atmosphere and low vacuum to minimize exposure to humidity. The use of a solution of liquid ammonia in dichloromethane for the amination reaction is also an important feature of this invention since it allows the addition of a more precise amount of aminating agent. When the tosylating agent is tosyl chloride, the ratio of cytidine to uridine at the end of amination is in the range of 12-15 to 1.

The selective extraction employed in this invention to remove the uridine byproducts represents an important achievement for the large scale preparation of cytidine nucleosides starting from uridine derivatives, since this was previously accomplished only by column chromatography.

Thus, selective extraction efficiently removes uridine derivatives from the reaction solution. The deprotection step can be carried out having a maximum of 2% or uridine derivative as contaminant in the solution, without compromising the purity of the final product.

In a specific embodiment of the present invention, the 2'-deoxycytidine nucleosides are prepared using the following steps.
  a) A 3'-acyl-deoxyribonucleoside is reacted with a solution of BOC-anhydride in a dry organic solvent, in the presence of a catalyst at controlled temperatures (23-26° C.). Preferred solvents for the reaction are chlorinated hydrocarbons, esters or ethers, preferably dichloromethane and/or ethyl acetate, in amounts varying from 5 to 15 parts by volume per one part by weight of the starting nucleoside, more preferably 6, 7, or 8 parts. Preferred catalysts are substituted pyridines, preferably DMAP, in amounts varying from 1 to 10 mol %, more preferably 5 mol % per mole of the starting nucleoside.
  b) The reaction solution of a) is reacted with a sulfonate such as p-toluenesulfonyl chloride in the presence of potassium carbonate sesquihydrate and DMAP-tosylate at 25-27° C.
  c) The salts are filtered and the reaction solution is diluted with dichloromethane followed by reaction with ammonia at 18-22° C.
  d) The cytidine derivative is purified by selective extraction of the uridine derivative with mixture of organic solvents upon conversion of the cytidine derivative to its hydrochloric salt. Preferred combination of polar solvents is water and methanol within the range of about 1:1 to about 5:1, by volume, more preferably a gradient proportion from 1.5:1 to 3:1. Preferred combination of non-polar solvents is hexanes and ethyl acetate within the range of about 4:1 to 2:1, by volume, more preferably a gradient proportion from 3:1 to 2:1.

e) A methanolic solution of the cytidine derivative is reacted with HCl, from 3 to 6 equivalents, more preferably 4 equivalents, at 33-35° C.

f) The product is crystallized with the addition of ethyl acetate.

5. Method for the Preparation of 5'—O-aminoacyl Derivatives of 2'-deoxy-β-L-nucleosides reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

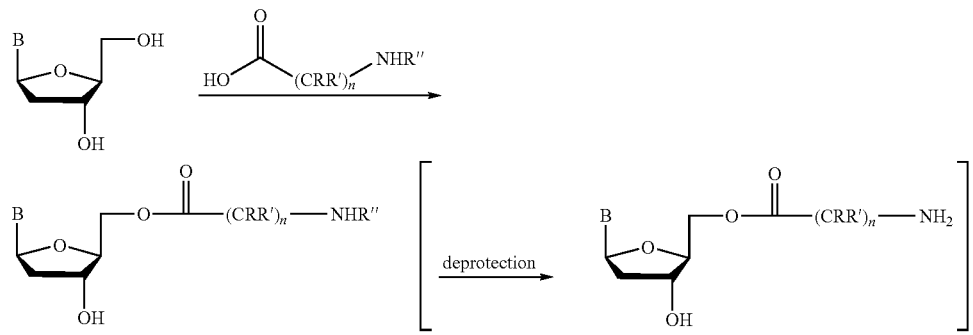

The key starting material for this process is an appropriately substituted 2'-deoxy-β-D or β-L nucleoside. The 2'-deoxy-β-D or β-L nucleoside can be purchased or can be prepared by any known means including standard coupling reactions with D or L deoxyribose. The title compounds then can be made by selectively coupling an amino acid to 2'-deoxy-β-L-nucleosides without any protection of the nucleoside.

6. Method for the Preparation of 3'—O-aminoacyl Derivatives of 2'-deoxy-β-L-nucleosides The key starting material for this process is also an appropriately substituted 2'-deoxy-β-D or β-L nucleoside. The 2'-deoxy-β-D or β-L nucleoside can be purchased or can be prepared by any known means including standard coupling reactions with D or L deoxyribose.

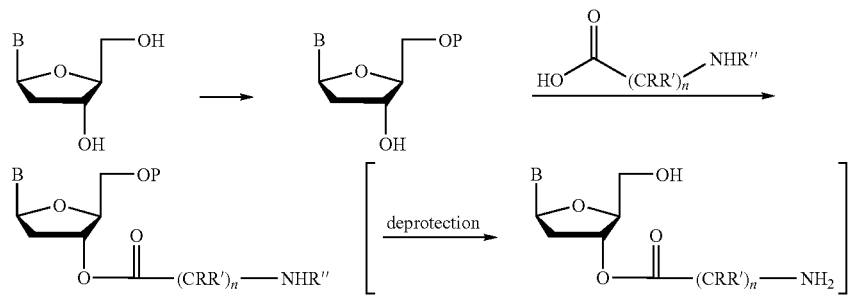

The coupling reaction can be achieved using appropriate coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the The title compounds can be made by first selectively protecting the 5'-hydroxyl with a suitable oxygen protecting group, such as an acyl or silyl protecting group, and optionally protecting any free amino in the heterocyclic or heteroaromatic base. Subsequently, the free 3'-hydroxyl can be coupled to a N-protected α or β amino acid.

The coupling reaction can be achieved using appropriate coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

7. Method for the Preparation of 3′,5′-bis-O-aminoacyl Derivatives of 2′-deoxy-β-L-nucleosides The key starting material for this process is also an appropriately substituted 2′-deoxy-β-D or β-L nucleoside. The 2′-deoxy-β-D or β-L nucleoside can be purchased or can be prepared by any known means including standard coupling reactions with D or L deoxyribose.

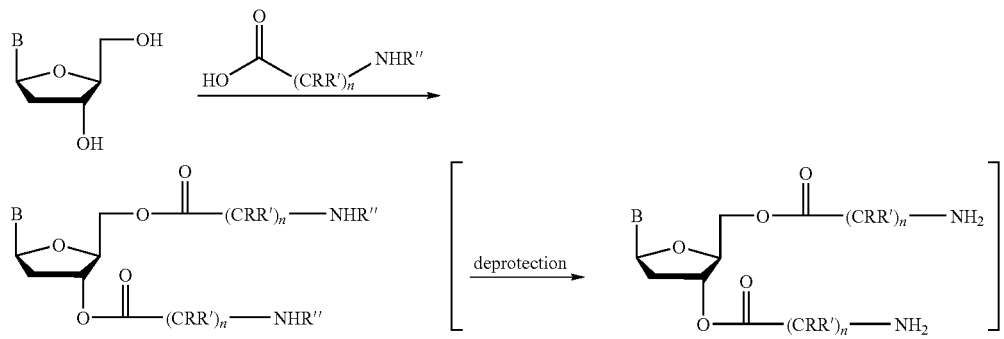

The protection can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

Subsequently, the free 3′-hydroxyl can be coupled to a N-protected α or β amino acid. The coupling reaction can be achieved using appropriate coupling reagents that promote the coupling. Some non-limiting examples of coupling reagents are Mitsunobu-type reagents (e.g. dialkyl azodicarboxylates such as diisopropyl azodicarboxylate and diethyl azodicarboxylate) with triphenyl phosphine or various types of carbodiimides.

The coupling reaction can be carried out at any temperature that achieves the desired results, i.e., that is suitable for the reaction to proceed at an acceptable rate without promoting decomposition or excessive side products.

Any reaction solvent can be selected that can achieve the necessary temperature and that can solubilize the reaction components. Non-limiting examples are any aprotic solvent including, but not limiting to, alkyl or halo-alkyl solvents such as hexane, cyclohexane, dichloromethane or dichloroethane, toluene, acetone, ethyl acetate, dithianes, THF, dioxane, acetonitrile, diethyl ether, pyridine, dimethylformamide (DMF), dimethylsulfoxide (DMSO), dimethylacetamide, or any combination thereof.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Although the invention has been shown and described with respect to exemplary embodiments thereof, various other changes, omissions, and additions in form and detail thereof may be made therein without departing from the spirit and scope of the invention.

While the invention has been described in connection with a preferred embodiments, it is not intended to limit the scope of the invention to the particular form set forth, but on the contrary, it is intended to cover such alternatives, modifications, and equivalents as may be included within the spirit and scope of the invention as defined by the appended claims.

This invention is further illustrated in the following sections. The working examples contained therein are set forth to aid in an understanding of the invention. The following examples are illustrative of the processes and products of the present invention; but this section is not intended to, and should not be interpreted to, limit in any way the invention set forth in the claims that follow thereafter. Equivalent, similar, or suitable solvents, reagents, or reaction conditions may be substituted for those particular solvents, reagents, or reaction conditions described herein without departing from the general scope of the method of synthesis.

EXAMPLES

Example 1

2-deoxy-L-ribose methyl glycoside

The starting materials include 2-deoxy-L-ribose, 27 Kg; methyl alcohol, 189 Lt; methanesulfonic acid, 0.27 Lt; dimethylaminopyridine, 2.46 Kg; toluene, 55 Lt.; ethyl acetate, 28 Lt.

To conduct the methyl glycoside formation, methanol, 162 Lt, is charged into the reactor with stirring. Then the starting sugar, L-2-deoxyribose, 27 Kg, is dissolved in the methanol and the temperature maintained at 25-30C. Next the acid catalyst methanesulfonic acid, MSA, 0.27 Lt, is dissolved in methanol, 27 Lt, and added.

The reaction is followed by thin layer chromatography to confirm complete transformation (usually 15-30 minutes) (tlc DCM/MeOH, 9:1). The acid catalyst is then quenched by addition of dimethylamino pyridine, DMAP, 2.46 Kg. The reaction medium is stirred for about 30 minutes at which time the pH is confirmed to be about 9.

The methanol is distilled under vacuum taking care to hold the temperature below 50° C. When distillation is ended toluene, 27 Lt, is then introduced and the vacuum distillation continued until it stops. Two additional distillations with toluene (14 Lt) are required to assure removal of residual methanol. Then the mixture is distilled twice with ethyl acetate (14 Lt).

In-process analysis: water (Karl Fischer) is under 0.1%. Methanol is not detected (as shown by the absence of p-methylbenzoic acid methyl ester when an aliquot of the mixture is allowed to react with p-toluoyl chloride).

Example 2

3,5—O-Ditoluoyl-2-deoxyribose methyl glycoside

The reagents include ethyl acetate, 108 Lt; toluoyl chloride, 55.8 Lt.; triethylamine, 66 Lt.

The protected methyl glycoside is produced by acylating the methyl glycoside of Example 1

The product from step 1 is dissolved in ethyl acetate, 54 Lt, and under argon, the contents are stirred and cooled to 3-5° C. Triethyl amine, TEA, 6 Lt, is added and cooling liquid is circulated at 3-5° C. Toluoyl chloride, 55.8 Lt, in ethyl acetate, 54 Lt, is then pumped into the above mixture at a rate such that the temperature of the reaction mixture does not rise above 15-17° C. This condition is maintained for the first 50% of the addition. After that, the cooling system is stopped and the addition continued allowing the reaction to achieve 32-35° C. Stirring is continued and the progress of the reaction is evaluated by tlc (hexane/ethyl acetate, 3/1) every two hours, and, when the reaction is apparently completed, evaluated by HPLC. Usual time is ca. 12 hours after addition of toluoyl chloride.

The resulting mixture is washed (stirred for 30 minutes) with an aqueous, 54 Lt, solution of sulfuric acid, 5.4 Lt, containing acetic acid, 0.54 Lt. The aqueous phase is extracted twice with methylene chloride, DCM (2×11 Lt) and the DCM extracts mixed with the main organic phase. The organic phase is washed with brine (2×34 Lt), and about 50% of the solvent is then distilled and the concentrate (107.3 Kg) is preserved for the next step.

Example 3

Chlorosugar

The reagents include the product from step 2, equivalent to 7.5 Kg of 2-deoxy-L-ribose; acetyl chloride, 30 Lt.; petroleum ether, 36 Lt.; methyl alcohol, 6 Lt.

The chloro sugar is produced by exposing the product of Example 2 to a collateral substitution reaction.

According to this discovery of the invention, a glass-lined reactor is charged with the ethyl acetate solution from step 2 containing the equivalent of 7.5 Kg of 2-deoxy-L-ribose. The ethyl acetate is removed by vacuum distillation (temperature in the jacket is 50° C.). The temperature of the mixture is lowered to 25° C. and the vacuum broken letting Argon into the reactor.

Following the ethyl acetate removal, acetyl chloride is charged to the reactor, 30 Lt, followed by pet. ether, 30 Lt. The mixture is stirred under argon and the temperature of the solution lowered to 8-10° C. Methanol, 6 Lt, in pet. ether, 6 Lt is then pumped in the reactor keeping the temperature between 8-10° C. Total time of addition is approximately 3.5-4 hours. When about 50% of the methanol has been added, massive precipitation is observed along with a raise in temperature to about 15-16° C. The temperature is allowed to go down to 8-10° C. and the addition of methanol continued. The reaction mixture is then stirred for 4 additional hours at 8-10° C. The reaction mixture contains a precipitate of the chloro sugar suspended in the organic solvent.

The product is filtered in a glass filter under an argon atmosphere. When the cake has settled, but not dried, the product is washed twice with pet. ether, 5 Lt. The cake is then suspended in pet. ether, 80 Lt, and stirred at 25° C. under argon for 10 minutes. The product is re-filtered and the cake is washed as before. When the filtration is completed, the vacuum is replaced by a current of argon that flows through the cake leading to complete elimination of solvents. The dried cake is then transferred to double polyethylene bags under argon and stored at 15° C. Yield is 17.7 Kg.

Compilation of more than 20 large scale batches (17-22 Kg) produced chloro-sugar with consistent specifications within the following limits:
Optical Rotation-(1% in DCM at 25C): −119 to −123.
Contents (HPLC): 95-97%.
Contents (argentometric titration of chloride): 97-98%

Example 4

Coupling of Chloro Sugar and Silylated Thymine to Produce Protected β-L-thymidine (L-TDT)

The reaction materials for this coupling reaction are as follows. Thymine, 41.8 Kg; ammonium sulfate 0.67 Kg; hexamethyldisilazane, 75 Lt; toluene, 42 Lt; chorosugar, 83.53 Kg; chloroform, 919 Lt; ethyl alcohol, 869 Lt The reactor is flushed with $N_2(g)$ for 10 minutes. Thymine (41.8 Kg), ammonium sulfate (0.67 Kg), 1,1,1,3,3,3-hexamethyldisilazane) (75 Lt), and toluene (42 Lt) are charged to the reactor. The reaction mixture is stirred and heated for 5-8 hours to a gentle reflux (jacket temp to 130° C.) (dissolution should have occurred). The reaction mixture is then cooled to 60° C. and the solvent is vacuum distilled while heating to 130° C. (this step removes excess 1,1,1,3,3,3-hexamethyldisilazane and toluene). Toluene (42 Lt) is charged and vacuum distilling continued, jacketed to 145° C. Reactor can be flushed with $N_2$ while vacuum distilling at 100° C. to drive off last traces if HMDS. Ideally this step produces a viscous, stirrable reaction mixture with a white layer on top, a sign that all HMDS has been eliminated. Gas chromatography can be used to ensure that all HMDS is eliminated.

When all HMDS is gone, the reaction mixture is cooled to 60° C. Ethanol free chloroform (835 Lt) is charged to reaction mixture under $N_2$ (g). The solution is stirred and cooled to 22° C. (+/−2° C.).

Then, 1-chloro-2-deoxy-3,5-di-O-toluoyl-L-ribose (83.53 Kg) at 22° C. (+/−2° C.) is charged with rapid, portionwise addition (0.5 min). Solutions of activated sugar should not be made before charging. The reaction mixture is stirred for 2.5 hours. Thin layer chromatography and HPLC are performed to ensure that the activated sugar is gone (TLC) and to assay for intermediate L-TDT (β/α=23).

When the spot of the activated sugar is not longer visible by TLC, the reaction mixture is stirred for 1 more hour at 22° C. (+/−2° C.). Then, celite (ca 41.86 Kg) is added, the slurry is cooled to 15° C. (+/−2° C) and ethanol (48 L) is slowly charged. The slurry is stirred for 30 minutes, then sodium bicarbonate (52 Kg) is added as a saturated aqueous solution (in ca 57 Lt water). The pH of the solution should be between 5-7.

The reaction mixture is filtered through a celite pad and the filter cake is washed 2×42 Lt of chloroform. The filtrate (clear) and washings and combined. Then water (90 Lt) is charged to filtrate. The contents are stirred for 30 min, agitation stopped and the contents allowed to settle for 10 min. HPLC is performed to assay disappearance of Thymine.

The contents are transferred for separation and bottom organic layer retained. The top aqueous layer is discarded as waste.

The organic layer is recharged to the reactor. Water (90 Lt) is charged to the reactor and the contents stirred for 30 min, agitation stopped and the contents allowed to settle for 10 min. The contents can be distilled under vacuum at ca. 60° C. The bottom organic layer is retained and the top aqueous layer discarded.

Most of the organic solvent is removed by vacuum distillation, then 95% ethanol (95 L) is charged to reactor with stirring at RT. The reaction mixture is stirred and heated to 60-70° C. for 0.5 hr. and then most of the solvent is removed by vacuum distillation. HPLC Analysis is performed for intermediate L-TDT. α-nucleoside: β-nucleoside 1:306.

Ethanol (678 Lt.) is charged to reaction mixture and stirred at 60° C. for 1 hour. The reaction mixture is cooled to 20° C. and stirred for 1 hour at this temperature. The reaction mixture is filtered and wash through with 95% ethanol (3×16 Lt). The solid is dried in a vacuum oven at 60° C./800 mbar to constant weight.

Yield=85.125 Kg (82.8%))

Example 5

Preparation of β-L-thymidine

Deprotection with sodium methoxide in methanol afforded pure L-dT in 95% yield.

Example 6

Coupling of Chloro Sugar and Silylated Uracil to Produce Protected β-L-2'-deoxyuridine (L-TDU)

A suspension consisting of uracil (5.35 Kg), hexamethyldisilazane (11.9 L), ammonium sulfate (93 g) and toluene (6.0 L) was heated at 140-150° C. until a clear solution was obtained (ca. 12 h). Toluene and excess $HMDS/NH_3$ were completely eliminated by distillation under reduced pressure. The silyluracil was transferred under argon to a 25-gallon glass-lined reactor containing 50 L of $CHCl_3$ and the silyluracil vessel rinsed with 20 L of $CHCl_3$. The cloudy solution was cooled to 22-25° C. and the solid sugar chloride (8.7 Kg) was added in one portion. The resulting suspension was stirred for ca 3 hours when TLC showed that the reaction was complete. HPLC Analysis showed total consumption of the chloro-sugar and the ratio β/α=12.

The reaction mixture was diluted with ethanol (15 L) and stirred for 30 minutes. The chloroform was distilled and the product crystallized from the reaction mixture. Water (80 L) was added and distillation was continued. The solid was collected by filtration and washed at 65° C. with water (2×80 L), ethanol (50 L), and water (2×80 L). The cake was filtered, washed with ethanol and dried in vacuum at 60-65° C.

Yield: 7.31 Kg (71%). HPLC Analysis of this intermediate showed the presence of 1.36% of the α-isomer.

Example 7

Preparation of β-L-Deoxyuridine

Deprotection with sodium methoxide in methanol afforded pure L-dU in 96% yield.

Example 8

Preparation of 5'—O-trityl-2'-deoxy-L-uridine (L-TRU)

A 100-gallon glass-lined reactor under argon was charged with 113 liters of dichloromethane, 11 liters of dry pyridine, 0.305 Kg of DMAP, 11.3 Kg of dry, milled 2'-deoxy-L-uridine, and 15.3 Kg of trityl chloride, and the mixture was heated to 30-34° C. with vigorous stirring for 12-16 hours. The heterogeneous mixture progressively became homogeneous. The progression of the reaction was monitored by TLC. Upon completion, the reaction was quenched with 900 mL of methanol and cooled to 24-28° C. The mixture was extracted twice with 38 L aqueous sulfuric acid solution (6.9 Kg conc sulfuric acid in 70 L of water) and once with 10% aqueous sodium bicarbonate (30 L). The mixture was then extract with water (30 L) until pH 5-6. The reactor jacket was then heated to 65° C. and 85% of the dichloromethane was distilled off. The concentrated mixture was cooled to 25-30° C. and diluted with 12 L of methyl isobutyl ketone under moderate stirring. The mixture was chilled to 8-10° C. for 2 hours. The crystalline mass was filtered and the solid was washed with cold dichloromethane (2-5 L), then dried in vacuo at 50° C. to constant weight to yield 19.18 Kg (81.6%) of 5'-Trityl-L-dU.

Example 9

Preparation of 5'—O-trityl-3'—O-(N-Boc-L-valyl)-2'-deoxy-L-uridine (LTBVU)

A 100-gallon glass-lined reactor under argon was charged with 133 liters of dichloromethane, 0.247 Kg of DMAP, 9.65 Kg of N-Boc-L-valine, and 19.0 Kg of dry, finely ground 5'—O-trityl-2'-deoxy-L-uridine, and the mixture was cooled to 10-14° C. with stirring. To a 25-gallon glass lined reactor under argon was added 19 L of dichloromethane and 10 Kg of DCC (melted at 40° C.). The DCC solution was slowly transferred to the 100-gallon reactor in such a rate to keep the internal temperature between 10 and 14° C. (1 to 2 hours). The progression of the reaction was monitored by TLC. Upon completion (2 to 3 hours), the reaction was filtered through filtering aid, and the solution extracted with aqueous sulfuric acid solution (1.37 L of concentrated sulfuric acid in 27.2 L of water), 10% aqueous sodium bicarbonate (27.2 L) until pH 5-6, and brine (30 L). The reactor jacket was then heated to 65° C. and 85% of the dichloromethane was distilled off. This concentrated solution can be used as such for the next step or the product can be seed to crystallize.

Example 10

Preparation of 3'—O-(N-Boc-L-valyl)-2'-deoxy-L-uridine (LBVU)

The concentrated solution obtained in Example 9 was cooled to 20-30° C. and the mercaptoethanol (3.12 L) and p-toluenesulfonic acid (0.57 Kg) were added under vigorous stirring. The reaction mixture was heated to 28-32° C. until TLC showed completion of the reaction (ca. 5 h). Then triethylamine (0.436 L) was added and the solution stirred for 30 min. The solution was extracted with 54 L of brine and the organic phase concentrated to a syrup. Xylene (51 L) was added to the concentrate and distillation of residual dichloromethane continued. Hexanes (51 L) was added and the suspension stirred for 30 min. The solid was filtered, washed with xylene/hexanes (1:1) until complete removal of non-polar impurities (ca. 5×). The solid is then dried in vacuo at 55° C. to constant weight to yield 14.95 Kg (87.4%) of 3'—O-(N-Boc-L-valyl)-L-dU.

Example 11

Preparation of 5'—O-Boc-3'—O-(N-Boc-L-valyl)-2'-deoxy-L-uridine (LBBVU)

A 25-gallon glass-lined reactor under argon was charged with 32 liters of dichloromethane, 5.29 Kg of LBVU, and 73 g of DMAP, under stirring at 23-26° C. With vigorous stirring, the mixture was cooled to 10-14° C. To a 10-gallon glass vessel under argon was added 11 L of dichloromethane and 2.7 Kg of di-t-butyl-dicarbonate and stirred at 22-25° C.). The di-t-butyl-dicarbaronate solution was slowly transferred to the 25-gallon reactor in such a rate to keep the internal temperature between 23 and 26° C. (1 to 2 hr). The progression of the reaction was monitored by TLC (10% MeOH in dichloromethane). Upon completion (2-3 hr) the reaction was immediately used in Example 12.

Example 12

Preparation of 5'—O-Boc-3'—O-(N-Boc-L-valyl)-2'-deoxy-L-cytidine (LBBVC)

To the solution of LBBVU of Example 11 was added 3.96 Kg of milled, freshly prepared $K_2CO_3$ 1.5 $H_2O$ and the mixture stirred for 15 min at 23-26° C. Then DMAP tosylate (0.177 Kg) and tosyl chloride (2.4 Kg) were added and the mixture was vigorously stirred at 25-27° C. The progression of the reaction was monitored by TLC using hexanes/ethyl acetate/methanol (1:1:0.1). After seven hours the reaction mixture was filtered through filtering aid under weak vacuum and argon flow to minimize exposure to air and moisture. The salts were washed with dichloromethane (3×5 L). The dichloromethane solution and washings were combined in a 100-gallon glass-lined reactor under argon. After the addition of 32 L of dichloromethane, the solution was cooled to 3-5° C. and 2.1 L of liquid ammonia was added. The reactor was sealed and the reaction mixture slowly brought to 18-22° C. The reaction was complete in ten hours and analysis of the reaction mixture (HPLC) revealed a ratio of cytidine/uridine: 11.

Example 13

Selective Removal of Uridines and Other Non Basic Components

The reaction solution was heated to 28-30° C. and extracted twice with water and aqueous sulfuric acid until pH 6.5-7.0. The dichloromethane was distilled to ¼ of the volume and the reaction solution was diluted with methanol (27 L). Distillation was continued until complete removal of dichloromethane. The reaction solution was cooled to 10-15° C., acidified to pH 2 with diluted aqueous HCl solution and diluted with water (27 L). Water (19 Kg) was added, followed by ethyl acetate (9 Kg). The mixture was allowed to stir for 10 minutes at 10° C. Hexane (8.5 Kg), ethyl acetate (8.5 Kg), and water (12.5 Kg) were added; the mixture stirred for 15 minutes and then the phases were separated. The aqueous phase was treated once again as before, but the order of addition of the extracting solvents was changed to: hexane (8.5 Kg), water (12.5 Kg), and ethyl acetate (8.5 Kg). This latter operation was repeated once more and the resulting aqueous phase evaluated by HPLC. It was found that there was less than 2% of BOC-val-LdU. After clarification with charcoal, the reaction solution was treated with 10% sodium bicarbonate solution until pH 6.5-7.5. The aqueous solution was extracted with dichloromethane (33 L). The organic phase was washed with brine and the organic phase concentrated to a syrup. The reaction solution was diluted with methanol (37 L) and distillation was continued until complete removal of dichloromethane.

Example 14

Deprotection: Preparation of 3'—O-(N-Boc-L-valyl)-2'-deoxy-L-cytidine (LVC)

Methanol (15 L) was cooled to 10° C. and acetyl chloride (4.7 Kg) was slowly added so that the internal temperature was held at 15-18° C. (approx. 1-2 hr).

The hydrogen chloride solution was pumped into the reaction solution of Example 13, within 40 minutes, under argon. The reaction mixture was stirred overnight at 33-35° C. when TLC using ethyl acetate/methanol (3:1) showed that the reaction was complete. The reaction solution was cooled to 25-27° C. and ethyl acetate (15 L) was added. The reaction solution was gently stirred until the product crystallized. Then the suspension was cooled to 10° C. for 2 hours. The product was vacuum filtered under argon, washed with ethyl acetate and dried at 50° C. (vacuum) to constant weight (Yield: 2.97 Kg, 62%). This product analyzed for >99% (HPLC or chloride titration) and showed spectroscopic properties fully consistent with the proposed structure.

Example 15

4-(N,N-dimethylamino)pyridinium-4-toluenesulfonate (FIG. 1)

DMAP (6.1 g, 0.050 moles) was dissolved in CH2Cl2 (50 mL) and then TsOH monohydrate (8.5 g, 0.050 moles) was added with stirring. The reagents dissolved to give a pale yellow/tan solution. This was boiled down to about half the volume and then cyclohexane (~50 mL) was added. The salt precipitated as a sticky mass, but as the boiling was continued, and presumably the salt was being azeotropically dried, the crystals became light and free. The mixture was allowed to sit on the bench overnight. Then, the mixture was filtered, rinsed with cyclohexane and then dried on the pump (mechanical) to give a pale, cream colored solid.

The reagents and conditions are more explicitly described below in Table 1.

TsCl (solid) was then added. This resulted in a temperature rise of 2-3° C., not significant on this scale. The TLC (1:1 EtOAc-hexane) showed that tosylation was taking place immediately. After about 30 min it appeared that the reaction was almost half-complete. After stirring overnight, the reaction was complete by TLC analysis with all of the TsCl reacted. The reactor was emptied into a 2L Erlenmeyer flask and the solution was dried with anhydrous $Na_2SO_4$, treated with charcoal (2 g), and then clarified with Perlita. Subsequently, the compound was aminated in a 2L jacketed, cylindrical reactor fitted with gas inlet tube, mechanical stirrer, thermometer, argon inlet, and gas outlet, filled from the bottom with argon. The clarified solution of the tosylate was put into the reactor and the hexane (1L) was added. The jacket temperature was set for 9.5° C. to maintain the reaction temperature below 11° C. the reactor was maintained under an argon blanket during the period that was required to cool the solution to 10° C. When the solution had reached this temperature the introduction of $NH_3$ was started with as slow a stream as could be controlled. The flux of $NH_3$ was continued for 4 hours. At this time it could clearly be seen that the solution was saturated. After about 1 hr of reaction at this temperature there was a lot of white precipitate. Considerable Tosylate still remained as shown by TLC and a significant amount of uridine had formed. The reaction was allowed to proceed at 10° C. overnight. After stirring overnight, the TLC

TABLE 1

| Rxn | Reagent | Mol. Unit | | Wt./Vol calc | | Mol/pts | Wt/Vol used | | Mol/pts | Eq/Pts |
|---|---|---|---|---|---|---|---|---|---|---|
| A | DMAP | 122.2 | FW | 6.1 | g | 0.050 | 6.1 | g | 0.050 | 1.0 |
| | $CH_2Cl_2$ | 8.0 | parts | 48.8 | mL | 8 | 50.0 | mL | 8 | 8.0 |
| | TsOH-$H_2O$ | 190.2 | FW | 9.49 | g | 0.050 | 8.5 | g | 0.045 | 0.9 |
| | cyclohexane | 10.0 | FW | 61.0 | mL | 10 | 60.0 | mL | 10 | 9.8 |
| | DMAPH$^+$TsO$^-$ | 294.4 | FW | 14.7 | g | calc-obt | 0 | g | 0.0% | |

Example 16

3',5'-di-(N-Boc-L-valyl)-L-2'-deoxycytidine from 3',5'-di-(N-Boc-L-valyl)-L-2'-deoxy-uridine (FIG. 2)

A 2L jacketed reactor fitted with mechanical stirrer, addition funnel, thermometer, and bottom drain was charged with $CH_2Cl_2$ (500 mL). DMAPH$^+$TsO$^-$ was added followed by the di-Boc-Val-2'dU. Not all of the substrate dissolved in this amount of solvent. The hydrated $K_2CO_3$ was ground to a powder and then added, which cause a lot of the substrate to dissolve. The mixture was stirred for 30 min. at 22° C. The showed that the reaction was complete. The reactor was warmed to 20° C., and then the contents were filtered. The filtercake ($NH_4^+$ TsO) was rinsed with $CH_2Cl_2$ and then air dried; it amounted to 24.87 g (82%). The filtrate was then concentrated by evaporation to remove the excess $NH_3$. The filtered reaction solution was extracted with 0.1M HCl (4×100 mL) to remove excess DMAP and water. It was found that EtOAc is optimal solvent to put the material on the column.

The reagents and conditions are more explicitly described below in Table 2.

TABLE 2

| Rxn | Reagent | Mol. Unit | | Wt./Vol calc | | Mol/pts | Wt/Vol used | | Mol/pts | Eq/Pts |
|---|---|---|---|---|---|---|---|---|---|---|
| A | Di-Boc-Val-2'-dU, L-CyVal-1d-2 | 626.7 | FW | 100.0 | g | 0.160 | 100.0 | g | 0.160 | 1.00 |
| | $CH_2Cl_2$ | 6.0 | parts | 600.0 | mL | 6 | 600.0 | mL | 6 | 6 |
| | DMAPH$^+$OTs$^-$ | 294.4 | FW | 2.35 | g | 0.0080 | 2.36 | g | 0.0080 | 0.050 |
| | $K_2CO_3$:$H_2O$ - 1:5 (17.8% $H_2O$) | 165.2 | FW | 63.26 | g | 0.383 | 64.0 | g | 0.387 | 2.4 |
| | TsCl | 190.7 | FW | 36.52 | g | 0.191 | 36.0 | g | 0.189 | 1.2 |
| B | hexane | 10.0 | parts | 1000.0 | mL | 10 | 1000.0 | mL | 10 | 10 |
| | $NH_3$ (gas) | 22.4 | L/mol | 8.6 | L | 0.383 | 0 | L | 0.0000 | 0.00 |
| | 3',5'-diBoc-Val-2'-dC, crude | 625.7 | FW | 99.8 | g | calc-obt | 99.0 | g | 99.2% | |

Example 17

HPLC Assay Method for diBocValyl-2'-dC and diBocValyl-2'-dU

Analytical Parameters
HPLC Column: NOVAPAK C18-4 pm-3.9×150 mm (WATERS)
Mobile Phase:
Pump A: $KH_2PO_4$ 0.015M pH=3.30-3.50 (adjusted with $H_3PO_4$ 10% v/v); Pump B: Acetonitrile HLPC Grade
Mixer chamber Volume −0.5 mL
Gradient pattern

| # | Time | Module | Event | Volume | Comment |
|---|------|--------|-------|--------|---------|
| 1 | 0.01 | Pumps | T. Flow | 1 | |
| 2 | 0.01 | Pumps | B. Conc. | 45 | |
| 3 | 12.00 | Pumps | B. Conc. | 45 | |
| 4 | 20.00 | Pumps | B. Conc. | 70 | |
| 5 | 28.00 | Pumps | B. Conc. | 70 | |
| 6 | 28.00 | Pumps | B. Conc. | 45 | |
| 7 | 32.00 | Pumps | B. Conc. | 45 | |
| 8 | 32.01 | SCL-10Avp | STOP | 0 | |
| 9 | | | | | |

Flow Rate: 1 ml/min
Column Temperature: 35° C.
Injection volume: 20 μL
Use the following wavelength for specific detection: 275 nm for di-Boc 2'dC, 260 nm for di-Boc2'dU and 204 for impurities after 15 minutes of run.

Sample Preparation
Prepare a sample solution in a concentration of ca./1.0 mg/mL using ethanol absolute as solvent. Dilute until a concentration of ca./0.16 mg/mL using (50%) (MeOH) /(50%) ($KH_2PO_4$ 0.015M pH=3.30-3.50) as solvent.

In one embodiment, the sample is stored in an inert atmosphere, such as under argon or nitrogen. In another embodiment, the solvents are degasified before use. In yet another embodiment, the sample is injected immediately after preparation.

Example 18

HPLC Assay Method For dival-L-dC-2HCl

Analytical Parameters
HPLC Column: HYPERSIL BDS C18-5 pm-4.6×250 mm (PHASE SEPARATION)
Mobile Phase:
Pump A: TEAAc 20 mM pH=6.20-6.30 (adjusted with acetic acid or trietilamine); Pump B: acetonitrile HLPC Grade
Mixer chamber Volume-0.5 mL
Gradient Pattern

| # | Time | Module | Event | Volume | Comment |
|---|------|--------|-------|--------|---------|
| 1 | 0.01 | Pumps | B. Conc. | 10 | |
| 2 | 0.01 | Pumps | T. Flow | 1 | |
| 3 | 5.00 | Pumps | B. Conc. | 10 | |
| 4 | 30.00 | Pumps | B. Conc. | 60 | |
| 5 | 30.01 | SCL-10Avp | STOP | 0 | |
| 6 | | | | | |

Flow Rate: 1 ml/min
Column Temperature: 30° C.
Injection volume: 20 μL
Use the following wavelength for specific detection: 270 nm.

Sample Preparation *
Prepare a sample solution in a concentration of ca./1.0 mg/mL using mobile phase for pump A (see above) as solvent. Dilute until a concentration ca./0.5 mg/mL using mobile phase for pump A (see above).

In one embodiment, the sample is stored in an inert atmosphere, such as under argon or nitrogen. In another embodiment, the solvents are degasified before use. In yet another embodiment, the sample is injected immediately after preparation.

All publications, patents, and patent documents are incorporated by reference herein, as though individually incorporated by reference. The invention has been described with reference to various specific and preferred embodiments and techniques. However, it should be understood that many variations and modifications will be obvious to those skilled in the art from the foregoing detailed description of the invention and may be made while remaining within the spirit and scope of the invention.

We claim:

1. A process for the preparation of β-L-2'-deoxythymidine comprising the steps of:
    (a) reacting a L-2-deoxyribose with an alcohol to form a L-1-O-alkyl-2-deoxyribose;
    (b) protecting the remaining free hydroxyls of the L-1-O-alkyl-2-deoxyribose to form protected L-1-O-alkyl-2-deoxyribose;
    (c) reacting the protected L-1-O-alkyl-2-deoxyribose with an anhydrous acid halide to form a protected L-1-halo-2-deoxyribose, wherein the anhydrous acid halide is produced in situ by the reaction of an acyl halide with a sub-equivalent amount of a second alcohol;
    (d) coupling the protected L-1-halo-2-deoxyribose with silylated thymine in chloroform to form a protected β-L-2'-deoxythymidine and a protected α-L-2'-deoxythymidine, wherein the ratio of the silylated thymine to the protected L-1-halo-2-deoxyribose is at least 1:1 and wherein the ratio of the protected β-L-2'-deoxythymidine to the protected α-L-2'-deoxythymidine is greater than about 10:1; and then
    (e) deprotecting the protected β-L-2'-deoxythymidine to obtain a β-L-2'-deoxythymidine.

2. The process of claim 1, wherein the silylated thymine is added in excess.

3. The process of claim 2, wherein the silylated thymine is added in a 2 molar excess.

4. A process for the preparation of β-L-2'-deoxyuridine comprising the steps of:
    (a) reacting a L-2-deoxyribose with an alcohol to form a L-1-O-alkyl-2-deoxyribose;
    (b) protecting the remaining free hydroxyls of the L-1-O-alkyl-2-deoxyribose to form a protected L-1-O-alkyl-2-deoxyribose;
    (c) reacting the protected L-1-O-alkyl-2-deoxyribose with an anhydrous acid halide to form protected L-1-halo-2-deoxyribose, wherein the anhydrous acid halide is produced in situ by the reaction of an acyl halide with a sub-equivalent amount of a second alcohol;
    (d) coupling the protected L-1-halo-2-deoxyribose with silylated uracil in chloroform to form a protected β-L-2'-deoxyuridine and a protected α-L-2'- deoxyuridine, wherein the ratio of the silylated uracil to the protected L-1-halo-2-deoxyribose is at least 1:1 and wherein the ratio of the protected β-L-2'-deoxyuridine to the protected α-L-2'-deoxyuridine is greater than about 10:1; and then (e) deprotecting the protected β-L-2'-deoxyuridine to obtain a β-L-2'-deoxyuridine.

5. The process of claim 4, wherein the silylated uracil is added in excess.

6. The process of claim 5, wherein the silylated uracil is added in a 2 molar excess.

7. The process of claim 1 or 4, wherein the alcohol is ethanol.

8. The process of claim 1 or 4, wherein the alcohol is methanol.

9. The process of claim 1 or 4, wherein the L-2-deoxyribose is reacted with an alcohol in the presence of an acid.

10. The process of claim 9, wherein the acid is an organic sulfonic acid.

11. The process of claim 10, wherein the acid is toluene sulfonic acid.

12. The process of claim 10, wherein the acid is methyl sulfonic acid.

13. The process of claim 9, wherein the acid is a carboxylic acid.

14. The process of claim 1 or 4, wherein an acid scavenger is used to quench the acid after formation of the L-1-O-alkyl-2-deoxyribose is complete.

15. The process of claim 14, wherein the acid scavenger is selected from the group consisting of triethylamine, pyridine and dimethylaminopyridine.

16. The process of claim 1 or 4, wherein the remaining free hydroxyls are protected with an acyl group.

17. The process of claim 16, wherein the acyl group is toluoyl.

18. The process of claim 1 or 4, wherein the acid halide is an acid chloride.

19. The process of claim 18, wherein the acid chloride is acetyl chloride.

20. The process of claim 1 or 4, wherein the second alcohol is methanol.

21. The process of claim 1 or 4, wherein the protected L-1-halo-2-deoxyribose crystallizes as it forms.

22. The process of claim 1, wherein the protected β-L-2'-deoxythymidine is deprotected by reaction with sodium methoxide in methanol.

23. The process of claim 4, wherein the protected β-L-2'-deoxyuridine is deprotected by reaction with sodium methoxide in methanol.

* * * * *

UNITED STATES PATENT AND TRADEMARK OFFICE
CERTIFICATE OF CORRECTION

PATENT NO. : 7,582,748 B2  Page 1 of 1
APPLICATION NO. : 10/806296
DATED : September 1, 2009
INVENTOR(S) : Jamie A. Rabi It is certified that error appears in the above-identified patent and that said Letters Patent is hereby corrected as shown below:

On the Title page, Item (73) Assignee: please

Delete "Microbiologica Quimica E Farmaceutical Ltd., Rio de Janeiro (BR)"

and insert -- Microbiologica Quimica E Farmaceutica Ltd., Rio de Janeiro (BR) --

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,582,748 B2
APPLICATION NO. : 10/806296
DATED : September 1, 2009
INVENTOR(S) : Jaime A. Rabi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 149 days.

Signed and Sealed this

Fourteenth Day of September, 2010

David J. Kappos
*Director of the United States Patent and Trademark Office*